United States Patent
Prost et al.

(10) Patent No.: US 11,324,611 B2
(45) Date of Patent: May 10, 2022

(54) SPRING DESIGN FOR PROSTHETIC APPLICATIONS

(71) Applicant: Massachusetts Institute of Technology, Cambridge, MA (US)

(72) Inventors: Victor Prost, Saint Didier (FR); Amos G. Winter, Somerville, MA (US); Kathryn Michelle Olesnavage, Ferndale, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 88 days.

(21) Appl. No.: 16/482,843

(22) PCT Filed: May 8, 2018

(86) PCT No.: PCT/US2018/031493
§ 371 (c)(1),
(2) Date: Aug. 1, 2019

(87) PCT Pub. No.: WO2018/208714
PCT Pub. Date: Nov. 15, 2018

(65) Prior Publication Data
US 2019/0350729 A1    Nov. 21, 2019

Related U.S. Application Data

(60) Provisional application No. 62/503,031, filed on May 8, 2017.

(51) Int. Cl.
*A61F 2/66* (2006.01)
*A61F 2/50* (2006.01)
(Continued)

(52) U.S. Cl.
CPC ...... *A61F 2/6607* (2013.01); *A61F 2002/503* (2013.01); *A61F 2002/5083* (2013.01);
(Continued)

(58) Field of Classification Search
CPC .............. A61F 2/6607; A61F 2002/503; A61F 2002/5072; A61F 2002/5083; A61F 2002/6671; A61L 27/08; A61L 27/10
See application file for complete search history.

(56) References Cited

U.S. PATENT DOCUMENTS 1,996,874 A  *  4/1935  Mascau ................. A61F 2/6607
                                                              623/49
4,364,128 A  *  12/1982  Mummert ................. A61F 2/66
                                                              623/38

(Continued)

OTHER PUBLICATIONS

European Patent Office, International Search Report and Written Opinion for PCT application No. PCT/US2018/031493, dated Jul. 11, 2018 (14 pages).

*Primary Examiner* — Yashita Sharma
*Assistant Examiner* — Melissa A Hoban
(74) *Attorney, Agent, or Firm* — Hamilton, Brook, Smith & Reynolds, P.C.

(57) ABSTRACT

A prosthesis, including a prosthetic foot, a prosthetic talocrural joint, a prosthetic ankle pivotally coupled to the prosthetic foot and a four-area bending beam. The four-area bending beam includes a U-shaped or other spring. One end of the spring is mechanically coupled via two of the four areas to the prosthetic foot. The other end of the spring is mechanically coupled via the other two areas to the prosthetic ankle. The spring resiliently resists pivoting of the prosthetic ankle about the prosthetic talocrural joint. The four-area bending beam exhibits an at least approximately constant moment along its length to maximize strain energy density, storing about four times as much elastic energy as a comparable cantilevered beam, thereby providing high stiffness and high range of motion to the ankle. The spring is modular, being easily replaced with another spring exhibiting a different stiffness, ex., to tailor the prosthesis to a user.

19 Claims, 16 Drawing Sheets

(51) Int. Cl.
*A61L 27/08* (2006.01)
*A61L 27/10* (2006.01)

(52) U.S. Cl.
CPC ....... *A61F 2002/6671* (2013.01); *A61L 27/08* (2013.01); *A61L 27/10* (2013.01)

(56) References Cited

U.S. PATENT DOCUMENTS

| | | | |
|---|---|---|---|
| 5,139,525 | A | 8/1992 | Kristinsson |
| 5,314,499 | A | 5/1994 | Collier, Jr. |
| 2002/0087216 | A1 | 7/2002 | Atkinson et al. |
| 2005/0038525 | A1* | 2/2005 | Doddroe .................. A61F 2/66 623/55 |
| 2006/0173555 | A1 | 8/2006 | Harn et al. |
| 2017/0056210 | A1* | 3/2017 | Jonasson ................ A61F 2/602 |

* cited by examiner

SPRING DESIGN FOR PROSTHETIC APPLICATIONS

CROSS REFERENCE TO RELATED APPLICATIONS

This application claims the benefit of U.S. Provisional Patent Application No. 62/503,031, filed May 8, 2017, titled "USpring Design for Prosthetic Applications," the entire contents of which are hereby incorporated by reference herein, for all purposes.

BACKGROUND

Technical Field

The present invention relates to prostheses and, more particularly, to spring designs for foot/ankle/joint prostheses.

Related Art

Humans require feet to stand and walk without assistance. Amputation of a foot significantly reduces a human's ability to stand and walk normally. Prostheses are, therefore, important for improving or restoring amputees' abilities in these areas. However, prior art passive prostheses do not accurately mimic dynamic mechanical characteristics of a normal human foot, such as dorsiflexion and energy return, which are particularly importing in walking.

Nearly two million people living in the United States have experienced limb loss, with the main causes being: vascular disease, including diabetes and peripheral arterial disease, (54%); trauma (45%); and cancer (less than 2%) [Ref 1]. Approximately 1,558 military personnel lost a limb as a result of wars in Afghanistan and Iraq. African-Americans are up to four times more likely to have an amputation than white Americans [Ref 2]. Approximately 185,000 amputations occur in the United States each year [Ref 3]. Below-knee amputations are the most common amputations, representing 71% of dysvascular amputations, with an expected 47% increase in below knee amputations from 1995 to 2020 [Ref 1].

SUMMARY OF EMBODIMENTS

An embodiment of the present invention provides a prosthesis. The prosthesis includes a prosthetic foot, a prosthetic talocrural joint, a prosthetic ankle pivotally coupled to the prosthetic foot by the prosthetic talocrural joint and a four-area bending beam. The four-area bending beam includes a first spring set. The first spring set includes at least one spring. A first terminal portion of each spring of the first spring set is mechanically coupled via two of four areas of the four-area bending beam to the prosthetic foot. A second terminal portion of each spring is mechanically coupled via the other two of the four areas of the four-area bending beam to the prosthetic ankle. The first spring set is configured to resiliently resist pivoting of the prosthetic ankle about the prosthetic talocrural joint, relative to the prosthetic foot.

Each spring of the first spring set may include a U-shaped spring, a C-shaped spring and/or a V-shaped spring.

Each spring of the first spring set may include nylon 6/6, carbon fiber and/or fiberglass.

The prosthetic foot may include a relatively rigid foot structure and a relatively flexible prosthetic forefoot cantilevered in front of the foot structure.

The prosthetic foot may also include a relatively flexible prosthetic heel.

The first spring set may be detachably attached to the prosthetic foot and to the prosthetic ankle, for example via respective removable pins.

The prosthesis may also include at least one first spring mount and at least one second spring mount. The at least one first spring mount may be mechanically coupled to the prosthetic foot, and the at least one second spring mount may be mechanically coupled to the prosthetic ankle. Each first spring mount of the at least one first spring mount may be configured to detachably receive a respective first terminal portion of a respective spring of the first spring set, and each second spring mount of the at least one second spring mount may be configured to detachably receive a respective second terminal portion of a respective spring of the first spring set.

Each spring of the first spring set may be detachably attached to the respective first and second spring mounts, for example via respective removable pins.

The prosthesis may include a kit of replacement spring sets. Each spring of the first spring set may have a respective stiffness, and the first spring set may have a total stiffness equal to a sum of the respective stiffnesses of the at least one spring of the first spring set. The prosthesis may include a plurality of selectable replacement spring sets. Each selectable replacement spring set of the plurality of selectable replacement spring sets may include at least one replacement spring. Each replacement spring may have a respective stiffness. Each selectable replacement spring set of the plurality of selectable replacement spring sets may have a respective total stiffness equal to a sum of the respective stiffnesses of the respective at least one replacement spring of the selectable replacement spring set. Each selectable replacement spring set may have a total stiffness different from the total stiffness of each other selectable replacement spring set and different from the total stiffness of the first spring set.

The prosthesis may also include at least one first spring mount and at least one second spring mount. The at least one first spring mount may be mechanically coupled to the prosthetic foot, and the at least one second spring mount may be mechanically coupled to the prosthetic ankle. Each first spring mount of the at least one first spring mount may be configured to detachably receive a respective first terminal portion of a respective spring of the first spring set, and each second spring mount of the at least one second spring mount may be configured to detachably receive a respective second terminal portion of a respective spring of the first spring set. Each first and second spring mount may be configured to detachably receive a respective first and second terminal portion of a selected respective replacement spring of the plurality of selectable replacement spring sets in replacement of the respective first and second terminal portion of the respective spring of the first spring set.

The total stiffness of a least stiff selectable replacement spring set of the plurality of selectable replacement spring sets may be at most about 2 N·m/deg., and the total stiffness of a most stiff selectable replacement spring set of the plurality of selectable replacement spring sets may be at least about 16 N·m/deg. For example, the plurality of selectable replacement spring sets may have respective stiffness of about 1.5, 2.9, 3.7, 5, and 24 N·m/deg.

The first four-area bending beam may have a substantially constant moment along its length.

The first spring set may include at least two springs. For example, the first spring set may include two, three, four, five or six springs.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Embodiments of the present invention provide a modular foot/ankle/joint prosthesis that provides high stiffness and high range of motion, thereby providing good dorsiflexion and energy return. A four-area bending beam in the prosthesis experiences an at least approximately constant moment (referred to herein as a "substantially constant moment") along its length to maximize strain energy density, storing up to four times as much elastic energy as a comparable cantilevered beam. A four-area bending beam, discussed in more detail below, is similar to a four-point bending beam. The prosthesis is modular, facilitating easy replacement of a spring or set of springs in the bending beam with another spring or set of springs having a different total stiffness, such as to tailor the prosthesis to a user.

Figure 1:
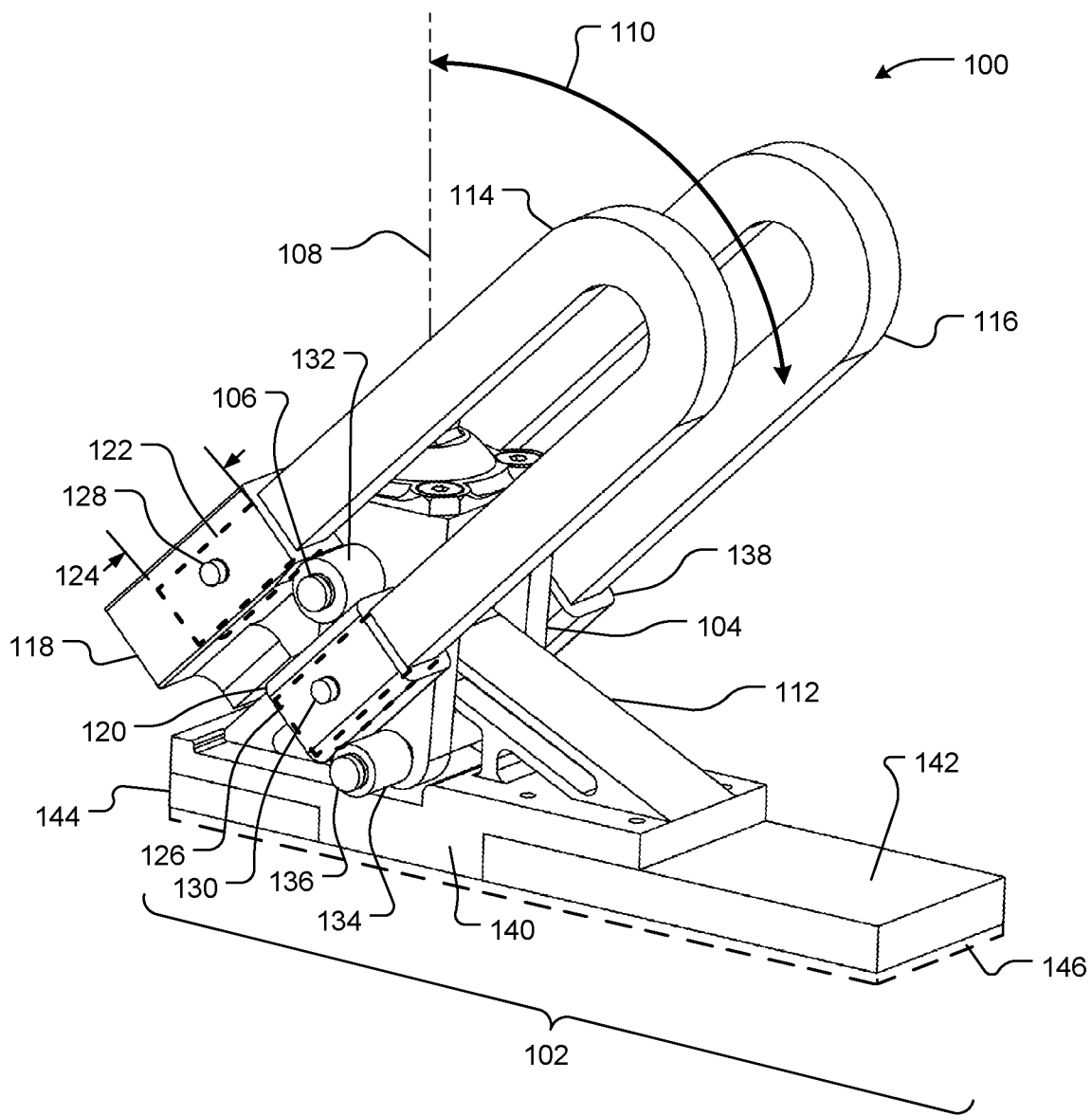
FIG. 1 is a perspective view of a prosthesis that includes a four-area bending beam that includes two U-shaped springs, according to an embodiment of the present invention.
Figure 2:
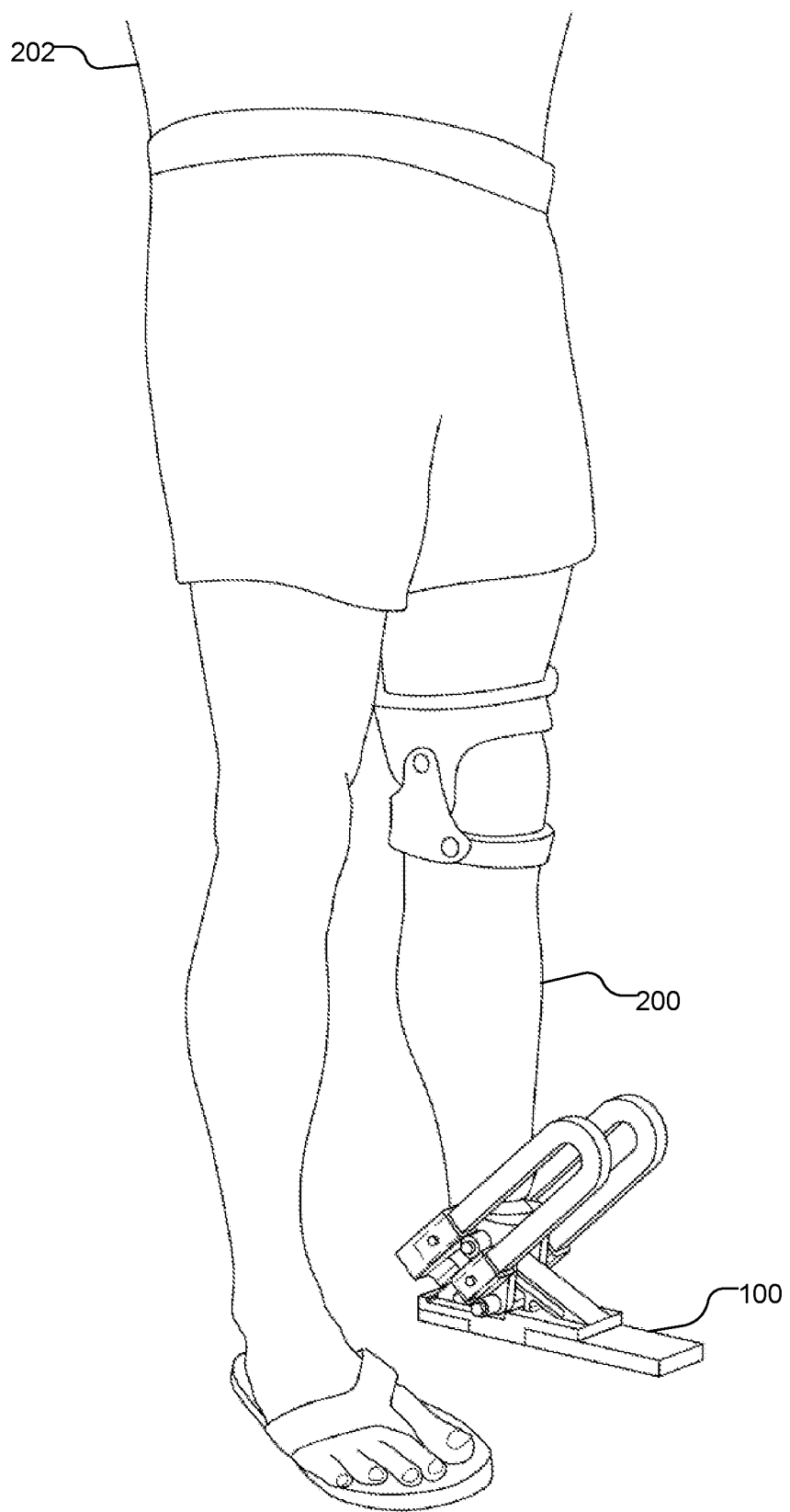
FIG. 2 is an illustration of the prosthesis of FIG. 1, fitted to a subject with a below-knee amputation, such as for testing the prosthesis, according to an embodiment of the present invention.

FIG. 1 is a perspective view of a prosthesis 100, according to an embodiment of the present invention. The prosthesis 100 includes a foot/ankle/joint complex. FIG. 2 illustrates an exemplary use of the prosthesis 100, in which the prosthesis 100 is attached to a leg stump socket 200 that may be worn by a human below-the-knee amputation subject 202. Embodiments of the present invention are not, however, limited to feet or to use by human subjects. For example, some embodiments may include other complexes of prosthetic components, and some embodiments may include prosthetic components for animals.

Returning to FIG. 1, the prosthesis 100 includes a prosthetic foot portion 102 (for simplicity, referred to herein as a prosthetic foot). A prosthetic ankle 104 is pivotally coupled to the prosthetic foot 102 via a pin 106, which acts as a prosthetic talocrural joint. The pin 106 may be made of steel or another suitable material. Thus, the prosthetic ankle 104 can pivot from a vertical axis 108, relative to the prosthetic foot 102, about the pin (prosthetic talocrural joint) 106, as indicated by an arrow 110, to permit dorsiflexion of the prosthetic foot 102. As used herein, "pivotally coupled" means mechanically coupled so as to provide rotational or approximately rotational motion in at least one dimension. The motion need not be purely rotational. The motion may, for example, include some parasitic motion, such as translation. Thus, in some embodiments, the prosthetic talocrural joint 106 may be implemented with a living hinge, cross-flexure joint or other flexure bearing. In some embodiments, the prosthetic talocrural joint 106 may be implemented with a ball and socket or any other suitable compliant joint that provides a pivotal coupling.

Figure 3:
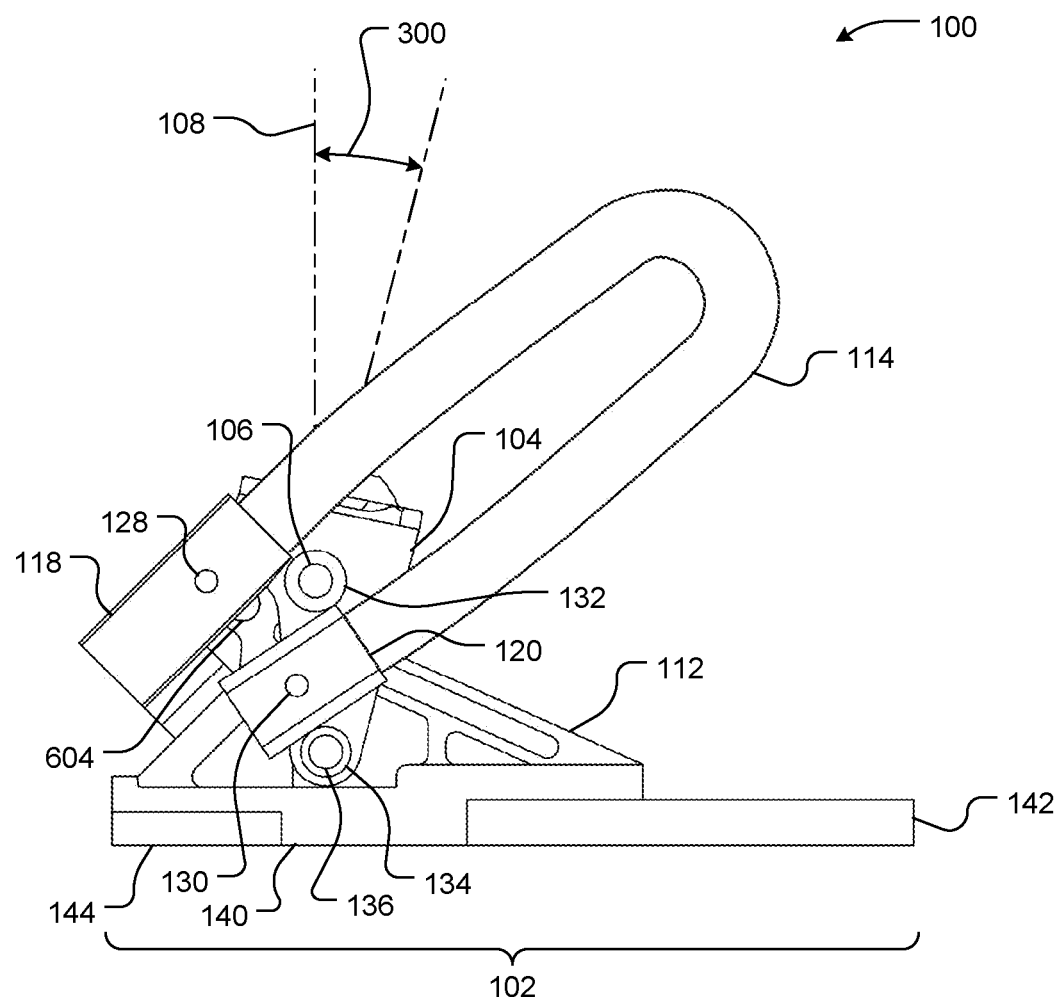
FIG. 3 is a side view of the prosthesis of FIGS. 1 and 2 illustrating resilient deformation of one of the U-shaped springs when a prosthetic ankle is bent, according to an embodiment of the present invention.
Figure 4:
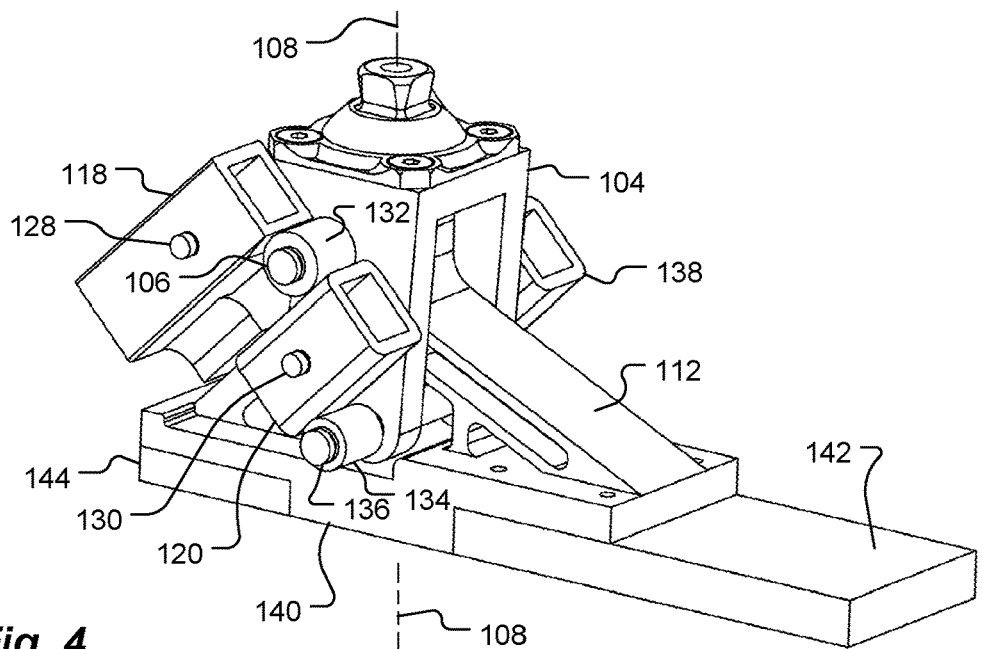
FIG. 4 is a perspective view of the prosthesis of FIGS. 1-3, with the U-shaped springs removed for clarity.
Figure 5:
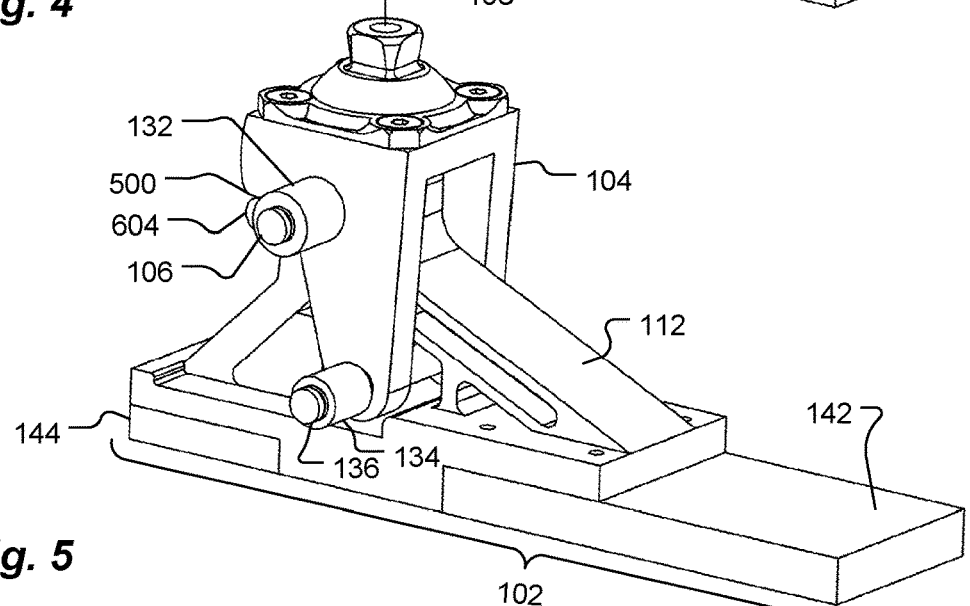
FIG. 5 is a perspective view of the prosthesis of FIGS. 1-4, with spring-end holding spring mounts also removed for clarity.
Figure 6:
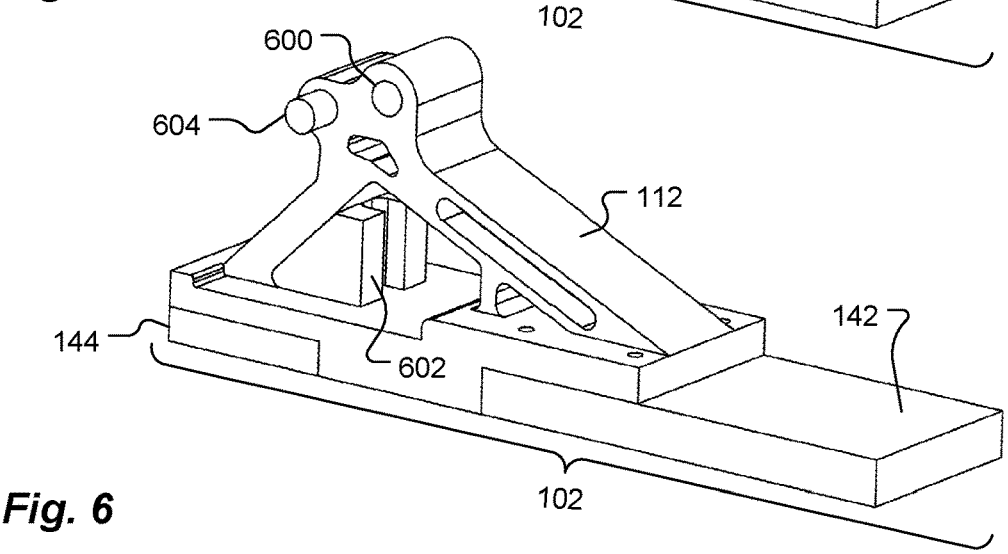
FIG. 6 is a perspective view of the prosthesis of FIGS. 1-5, with the prosthetic ankle also removed for clarity.
Figure 7:
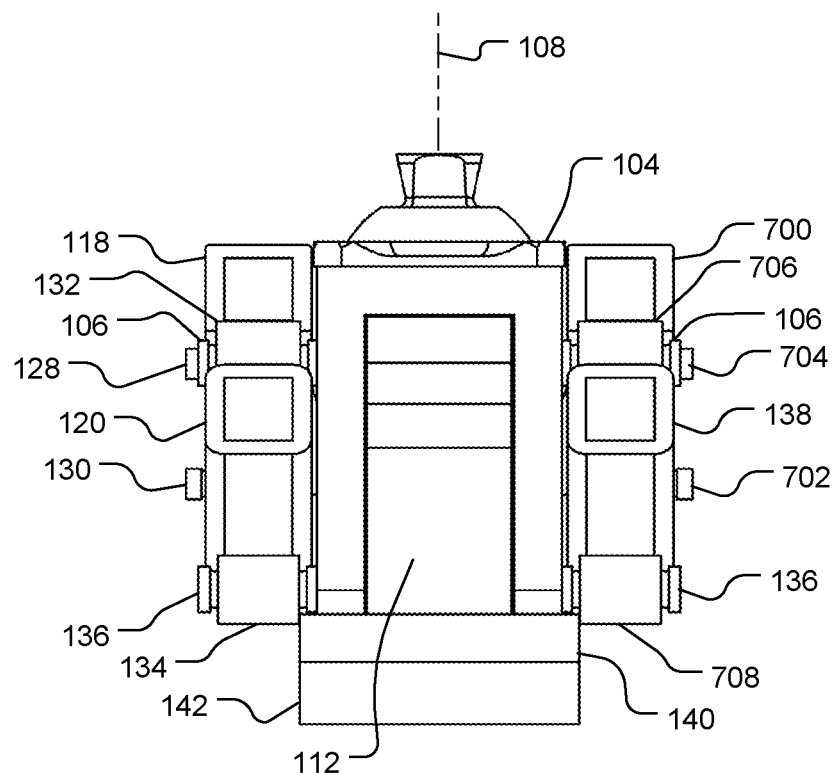
FIG. 7 is a front view of the prosthesis of FIG. 4.
Figure 8:
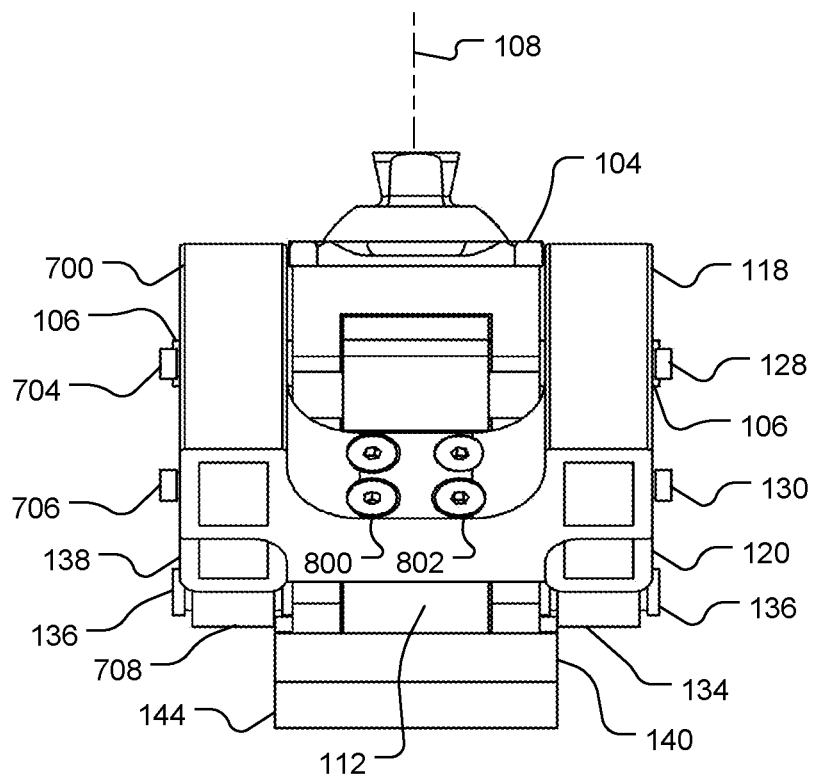
FIG. 8 is a rear view of the prosthesis of FIG. 4.

FIG. 3 is a side view of the prosthesis 100 with the prosthetic ankle 104 bent at an angle 300 from the vertical axis 108. FIGS. 4, 5 and 6 are respective perspective views, and FIGS. 7 and 8 are respective front and rear views, of the prosthesis 100, each with various components removed for clarity. The prosthetic foot 102 includes a riser section 112 (best seen in FIG. 6), which defines a hole 600, through which the pin 106 extends.

Returning again to FIG. 1, two U-shaped springs 114 and 116 (also referred to herein as U-shaped beams) are each mechanically coupled between the prosthetic foot 102 and the prosthetic ankle 104. The U-shaped springs 114 and 116 are configured to resiliently resist pivoting of the prosthetic ankle 104, from the vertical axis 108, about the prosthetic talocrural joint 106. The U-shaped springs 114 and 116 may be made of nylon 6/6, carbon fiber, fiberglass or another suitable material, as discussed in more detail herein.

Finite lengths of each end of the U-shaped spring 114 terminate within a respective spring mount 118 and 120 (see also FIG. 4). A terminal portion 122 (FIG. 1) of the U-shaped spring 114, shown in phantom, near one end of the U-shaped spring 114 has a length 124 and extends into the spring mount 118 by the length 124. Similarly, a terminal portion 126, shown in phantom, near the other end of the U-shaped spring 114 has a corresponding length and extends into the other spring mount 120 by the corresponding length. The terminal portions 122 and 126 can, but need not, be of equal lengths.

The terminal portions 122 and 126 of the U-shaped spring 114 may be permanently attached to the respective spring mounts 118 and 120. However, the terminal portions 122 and 126 are preferably detachably attached to the spring mounts 118 and 120, such as by respective removable pins 128 and 130. The removable pins 128 and 130 prevent the terminal portions 122 and 126 unexpectedly withdrawing from the spring mounts 118 and 120. However, making the U-shaped spring 114 selectively detachable facilitates replacing the U-shaped spring 114 with another spring having a different stiffness, as discussed in more detail herein.

The spring mounts 118 and 120 may be made of aluminum or another suitable material. One spring mount 118 may be rigidly attached, such as via screws, exemplified by screws 800 and 802 (FIG. 8), to a back portion of the riser section 112 of the prosthetic foot 102. Thus, the spring mount 118, and thereby one end of the U-shaped spring 114, is mechanically coupled to the prosthetic foot 102.

The other spring mount 120 (FIG. 1) is not necessarily rigidly attached to the prosthetic ankle 104 or to the prosthetic foot 102. Instead, the spring mount 120 may slide or ride on a bearing 132 on the pin 106. This spring mount 120 may, thus, be able to slide or ride along and part way around the bearing 132, as well as on or along another bearing 134 on a bottom shaft 136 attached to the prosthetic ankle 104 (see also FIGS. 3-5 and 7). Thus, although the spring mount 120 may not be rigidly attached to the prosthetic ankle 104 or to the prosthetic foot 102, mechanical contact between each of the two bearings 132 and 134 and the spring mount 120, the ability of the bearings 132 and 134 to slide or ride along and around the spring mount 120, and the consequential ability of the bearings 132 and 134 to exert force on the spring mount 120, and thereby exert force on the U-shaped spring 114, mechanically couple the end of the U-shaped spring 114 to the prosthetic ankle 104.

In some embodiments (not shown), both spring mounts 118 and 120 are rigidly attached to respective portions of the prosthesis 100.

The bottom shaft 136 is attached to, and swings with pivots of, the prosthetic ankle 104, as the prosthetic ankle 104 is bent and force is applied to the U-shaped springs 114 and 116 (FIG. 3). A mechanical stop 602 (FIG. 6) limits rearward travel of the bottom shaft 136 to set an upper limit on the bending angle 300 (FIG. 3) of the prosthetic ankle 104.

As the prosthetic ankle 104 returns to a vertical orientation, force is removed from the U-shaped springs 114 and 116. A pin 604 (best seen in FIG. 6, but also see FIGS. 5 and 3) prevents counterclockwise (as viewed in FIGS. 3, 5 and 6) rotation of the prosthetic ankle 104 beyond the vertical orientation, i.e., beyond the vertical axis 108. When the prosthetic ankle 104 is in the vertical orientation, a seat portion 500 (FIG. 5) of the prosthetic ankle 104 contacts the pin 604, preventing further counterclockwise rotation of the prosthetic ankle 104.

As with the U-shaped spring 114, terminal portions at each end of the other U-shaped spring 116 (FIG. 1) terminate within respective spring mounts 138 (see also FIG. 4) and 700 (FIGS. 7 and 8) and are detachably attached to the respective spring mount 138 or 700 with respective removable pins 702 and 704 (FIGS. 7 and 8). The spring mount 700 may be rigidly attached to the back portion of the riser section 112 by the screws 800 and 802 (FIG. 8). However, as with the spring mount 120, the other spring mount 138 is not necessarily rigidly attached to the prosthetic ankle 104 or to the prosthetic foot 102. Instead, the spring mount 138 may slide or ride on a bearing 706 (FIG. 7) on the pin 106. This spring mount 138 may, thus, be able to slide or ride along and around the bearing 706, as well as on or along another bearing 708 on the bottom shaft 136.

Figure 9:
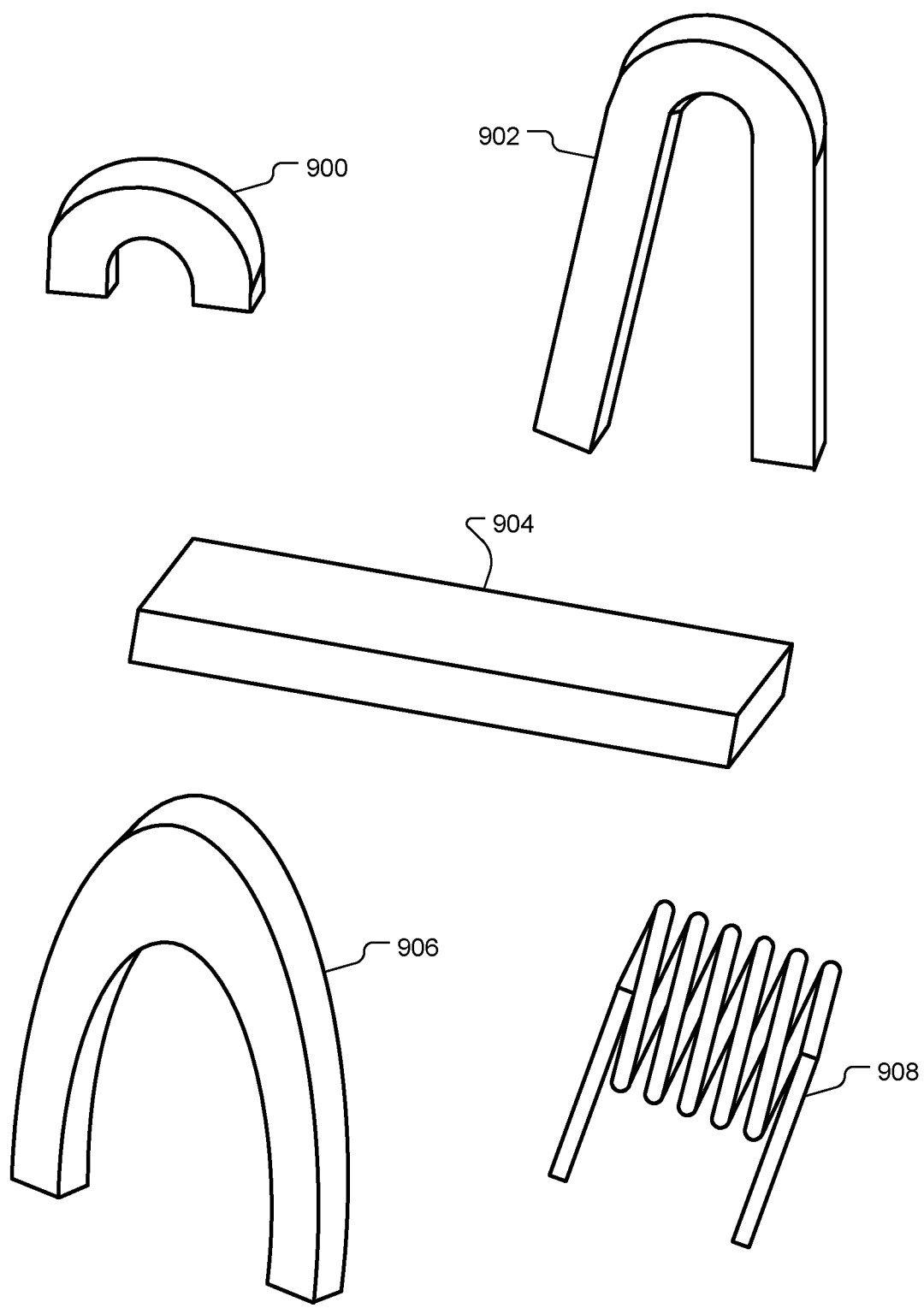
FIG. 9 is a perspective illustration of five other exemplary shapes of springs that may be used in a four-area bending beam of a prosthesis, according to respective embodiments of the present invention.

The U-shape of the springs 114 and 116 is merely exemplary. For example, in other embodiments, terminal portions, similar to the terminal portions 122 and 126, of each spring need not necessarily be parallel, as they are in the U-shaped springs 114 and 116. Furthermore, other numbers of springs, and other shapes of springs, may be used in other embodiments. For example, some embodiments include one spring, while some embodiments include more than two springs. Some embodiments include a C-shaped spring 900, a V-shaped spring 902, a straight bar-shaped spring 904, a curved beam, such as a non-circular, i.e., varying radius, arch 906 or a helix, such as a torsional helical spring 908, as illustrated in FIG. 9. Some embodiments include straight springs, while other embodiments include springs that have other shapes. Although some springs discussed herein are essentially planar, in some embodiments the springs curve in a z direction, such as in the case of the torsional helical spring 908.

In any case, each spring, exemplified by the springs 114 and 116 (FIG. 1) and 900 and 902 and 904 (FIG. 9), is part of a four-area bending beam. A four-area bending beam is similar to a four-point bending beam. Four-point bending beams and four-area bending beams are discussed in more detail below. A first end, for example the terminal portion 122 (FIG. 1), of the U-shaped spring 114 is mechanically coupled via a first two of the four areas to the prosthetic foot 102, and a second end, for example the terminal portion 126, of the U-shaped spring 114 is mechanically coupled via the other two of the four areas to the prosthetic ankle 104.

Although conventional four-point bending beams may be straight, as used herein a four-area bending beam may be curved, such as U-shaped. The curve need not lie in a plane. The terminal portion 122 of the U-shaped spring 114, i.e., the length of the U-shaped spring 114 that terminates within the spring mount 118, is sufficiently long to space apart the first two of the four areas along the length of the terminal portion 122. Similarly, the other terminal portion 126 of the U-shaped spring 114, i.e., the length of the U-shaped spring 114 that terminates within the spring mount 120, is sufficiently long to space apart the other two of the four areas along the length of the terminal portion 126.

Figure 10:
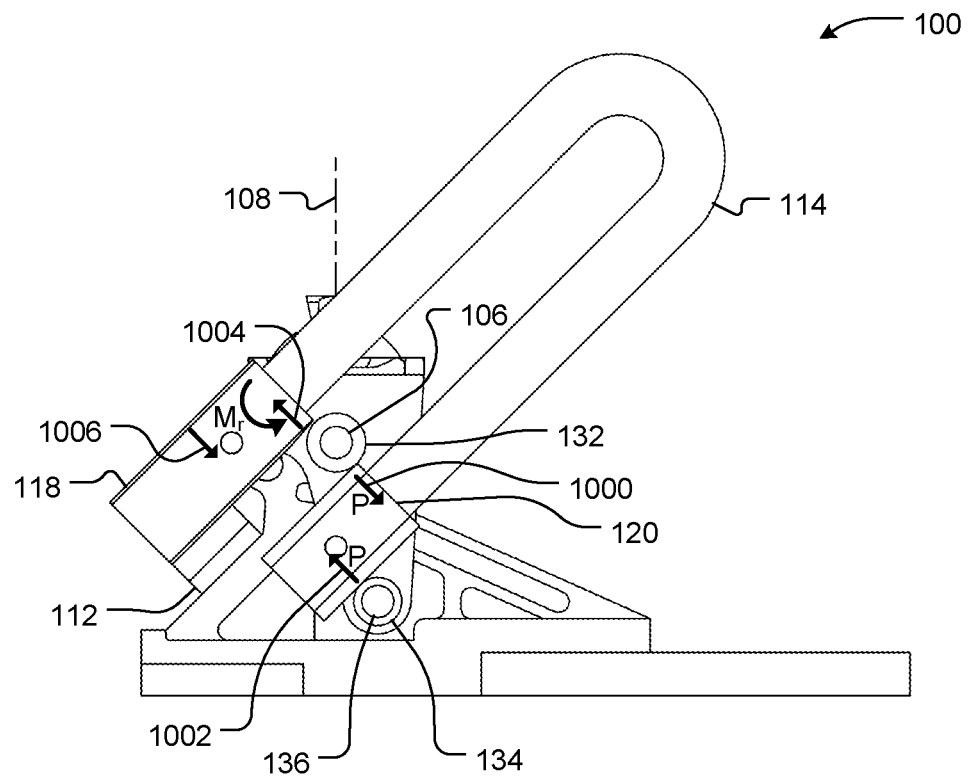
FIG. 10 is a side view of the prosthesis of FIGS. 1-3 schematically illustrating forces applied when the prosthetic ankle bends, according to an embodiment of the present invention.

As shown in FIG. 10, a force, indicated by an arrow 1000, applied through a mechanical contact between the bearing 132, driven by the pin 106, against the spring mount 120, and thereby against the U-shaped spring 114, corresponds to one area of the four-area bending beam. Another force, indicated by an arrow 1002, applied through a mechanical contact between the bearing 134, driven by the pin 136, against the spring mount 120, and thereby against the U-shaped spring 114, corresponds to a second area of the four-area bending beam. Yet another force, indicated by an arrow 1004, applied through a rigid connection between the riser portion 112 of the prosthetic foot 102 against the spring mount 118, and thereby against the U-shaped spring 114, corresponds to a third area of the four-area bending beam. A fourth force, indicated by an arrow 1006, applied through a rigid connection between the riser portion 112 of the prosthetic foot 102 against the spring mount 118, and thereby against the U-shaped spring 114, corresponds to a fourth area of the four-area bending beam.

As noted, the spring 114, 116, 900, 902 or 904 is configured to resiliently resist pivoting of the prosthetic ankle 104 about the prosthetic talocrural joint 106, relative to the prosthetic foot 102. Four-area bending beams are discussed in more detail below.

The prosthetic ankle 104 and rigid structural components of the prosthetic foot 102, such as the riser portion 112 of the prosthetic foot 102 and a portion of the prosthetic foot 102 below the riser portion 112, may be made of acetal resin or another suitable material. The prosthetic foot 102 may include a relatively rigid foot structure 140 and a relatively flexible prosthetic forefoot 142 cantilevered in front of the foot structure 140. The prosthetic forefoot 142 may be made of a material, such as an extruded or machined nylon (e.g., nylon 6/6 or polyhexamethylene adiptimide), that is flexible, relative to the relatively rigid foot structure 140. The prosthetic forefoot 142 may be attached to the foot structure 140 in any suitable way, such as by screws or an adhesive.

The prosthetic foot 102 may include a prosthetic heel 144 made of a yet more resilient material, such as rubber, to absorb impacts of heel-strike walking, and/or a material that provides suitable friction with anticipated walking surfaces. Optionally, the prosthetic foot 102 may include a resilient sole 146 (shown in dashed line), such as a rubber sole, or another material that provides suitable friction with anticipated walking surfaces.

A prototype of the prosthesis 100 exhibits a nearly constant rotational stiffness at the ankle $k_{ank}$ of about 3.7 N·m/deg, and a forefoot beam stiffness $k_{met}$ of about 16.0 N·m².

Prosthesis with Interchangeable Custom Springs for Evaluating Lower Leg Trajectory Error (LLTE)

An experimental prosthesis (referred to in the following description as a prosthetic foot) may be used for evaluating a design objective. This objective, called the Lower Leg Trajectory Error (LLTE), enables optimization of passive prosthetic feet by modeling trajectory of a shank during single support for a given prosthetic foot and selecting design variables that minimize error between this trajectory and able-bodied kinematics. A light-weight, fully-characterized test foot with variable ankle joint stiffness was designed to evaluate the LLTE. The test foot can replicate the range of motion of a physiological ankle over a range of different ankle joint stiffnesses.

The test foot includes a rotational ankle joint machined from acetal resin, interchangeable U-shaped nylon springs that range from about 1.5 N·m/deg to about 24 N·m/deg, and a flexible nylon forefoot with a bending stiffness of about 16 N·m². The U-shaped springs were designed to experience an at least approximately constant moment along their lengths to maximize strain energy density. This feature facilitated creating a high-stiffness and high-range-of-motion ankle.

The design performed as predicted during mechanical and in vivo testing, and its modularity allowed us to rapidly vary the ankle joint stiffness. Qualitative feedback from preliminary testing showed that this design is ready for use in large scale clinical trials to further evaluate the use of the LLTE as an optimization objective for passive prosthetic feet.

Introduction

Lower Leg Trajectory Error (LLTE) is an optimization metric that can be used to design passive prosthetic feet tailored to a subject's body mass and size. This metric, first proposed by the inventors in previous work [Ref 4], relates the mechanical attributes of a passive foot to the gait of an amputee. The metric involves modeling the trajectory of the lower leg segment (shank) throughout the single support phase of gait for a given prosthetic foot. The lower leg trajectory in the sagittal plane can be described by three variables: $x_{knee}$, $y_{knee}$, and $\theta_{LL}$. To compute the LLTE, these variables are compared to target physiological values taken from published gait data [Ref 5], $\hat{x}_{knee}$, $\hat{y}_{knee}$, and $\hat{\theta}_{LL}$. These variables are a set of discrete points taken at different time intervals. The normalization of the root-mean-square error was chosen to reduce the bias towards any of the kinematic variables and was done by using average values of each of the physiological parameters over the portion of the step included in the optimization, $\bar{x}_{knee}$, $\bar{y}_{knee}$, and $\bar{\theta}_{LL}$. The equation for computing the LLTE can thus be written as $$LLTE = \sqrt{\frac{1}{N}\sum_{n=1}^{N} \left(\frac{x_n^{knee} - \hat{x}_n^{knee}}{\bar{x}_{knee}}\right)^2 + \left(\frac{y_n^{knee} - \hat{y}_n^{knee}}{\bar{y}_{knee}}\right)^2 + \left(\frac{\theta_n^{LL} - \hat{\theta}_n^{LL}}{\bar{\theta}^{LL}}\right)^2} \quad (1)$$

where n refers to the nth time interval and N is the total number of time interval considered in a step.

The design can then be optimized by selecting mechanical and geometric values that minimize the error between this trajectory and target physiological lower leg kinematics. This method was previously used to optimize simple analytical prosthetic foot models including: (i) one with a pinned ankle and metatarsal joint, using constant rotational stiffnesses as design variables; and (ii) another with a pinned ankle joint and flexible forefoot, where rotational ankle stiffness and forefoot bending stiffness were the design variables [Ref 4].

Thus far, all work regarding LLTE has been purely theoretical. The next step in moving towards using the optimization metric to design commercial prosthetic limbs is to clinically test validity of LLTE as a design objective for prosthetic feet. One goal of our study included creation of an experimental prosthetic foot to test clinical viability of LLTE. The prototype prosthetic foot had to meet the following design requirements: (i) light enough that the weight of the foot does not affect gait kinematics over the duration of the test; (ii) fully mechanically characterized, such that the deformation of the foot under a given load can be calculated, thereby allowing evaluation of the LLTE value for the foot; (iii) modular so that at least one design variable can be altered during testing in order to compare gait kinematics across a range of values of that design variable, e.g., ankle stiffness or forefoot bending stiffness; and (iv) able to express ankle stiffnesses greater or less than a physiological ankle while reaching physiological ranges of motion.

Our previous prototypes were built using commercially available steel coil springs. These feet proved to be too heavy and large, and they did not allow spring interchangeability [Refs. 6, 7].

The design presented here includes a rotational ankle (talocrural) joint with interchangeable springs and a cantilever beam forefoot. The design variables of the architecture, i.e., rotational stiffness of the ankle and bending stiffness of the forefoot, were optimized using the LLTE. Considerations in building a physical prototype based on this theoretical design are discussed herein, and a resulting device is presented. Our technique of using an at least approximately constant moment spring to maximize strain energy storage and facilitate a high-stiffness, high-range-of-motion ankle may be of value to other researchers designing prosthetic feet. Mechanical testing results are included to show that the intended design specifications were satisfied. Qualitative feedback from preliminary user testing is also reported and discussed.

Lower Leg Trajectory Error Design Optimization Method

Figure 11:
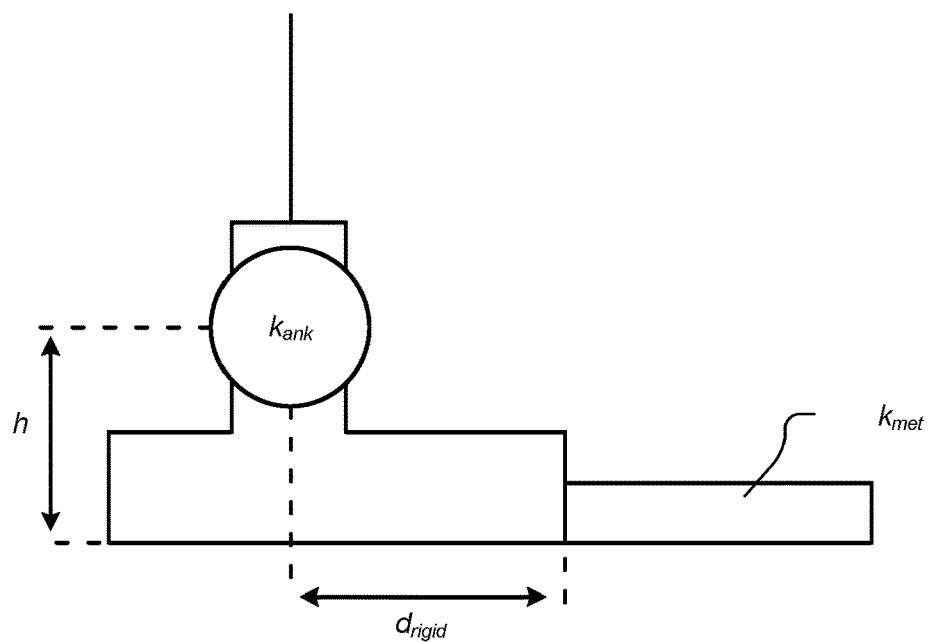
FIG. 11 is a schematic diagram of a foot architecture, including an ankle joint and a forefoot cantilevered beam, selected to replicate articulation of a physiological foot/ankle complex, according to an embodiment of the present invention.

A conceptual architecture of the experimental foot consists of a rotational ankle joint with constant stiffness $k_{ank}$ and a flexible forefoot modeled as a cantilever beam with a stiffness $k_{met}$ (see FIG. 11), as presented in previous LLTE work [Refs. 4, 7]. FIG. 11 is a schematic diagram of the foot architecture, including an ankle joint and a forefoot cantilevered beam. Positions of the ankle joint and the forefoot were chosen to replicate articulation of a physiological foot/ankle complex. Geometry of the rotational ankle and beam forefoot foot were selected to replicate articulation of a physiological foot/ankle complex from a set of published gait data, with an h of about 8.0 cm and a $d_{rigid}$ of about 9.3 cm [Ref 5]. The rigid structure length, $d_{rigid}$, was chosen such that the effective rotational joint of the pseudo-rigid-body model of the flexible forefoot during late stance would approximately coincide with the center of rotation of the metatarsal joint of a human foot. The pseudo-rigid-body model approximates a cantilever beam with a vertical end load as a rigid link and a rotational joint with stiffness related to the beam bending stiffness [Ref 8].

Values for the design variables, $k_{ank}$ and $k_{met}$, were optimized in prior work using the LLTE design optimization method [Ref 4]. This method works by imposing physiological ground reaction forces (GRFs), matching the subjects' masses and sizes, on a model prosthetic foot with given stiffness and geometry. The resulting deflection, and thus the trajectory of the shank, can be computed and compared to physiological kinematics using the LLTE error function (Eq. (1)). The stiffness of the ankle and forefoot can then be tuned to reduce the LLTE [Ref 1]. For this study, Winter's gait data for a subject of body mass 56.7 kg [Ref 5] were used as inputs into the LLTE design optimization method. The set of design variables giving the lowest value for LLTE was taken to be the optimal design. The minimum LLTE value, 0.222, was calculated for $k_{ank}$=3.7 N·m/deg and $k_{met}$=16.0 N·m².

Mechanical Design of a Foot Experimental Device

Figure 12:
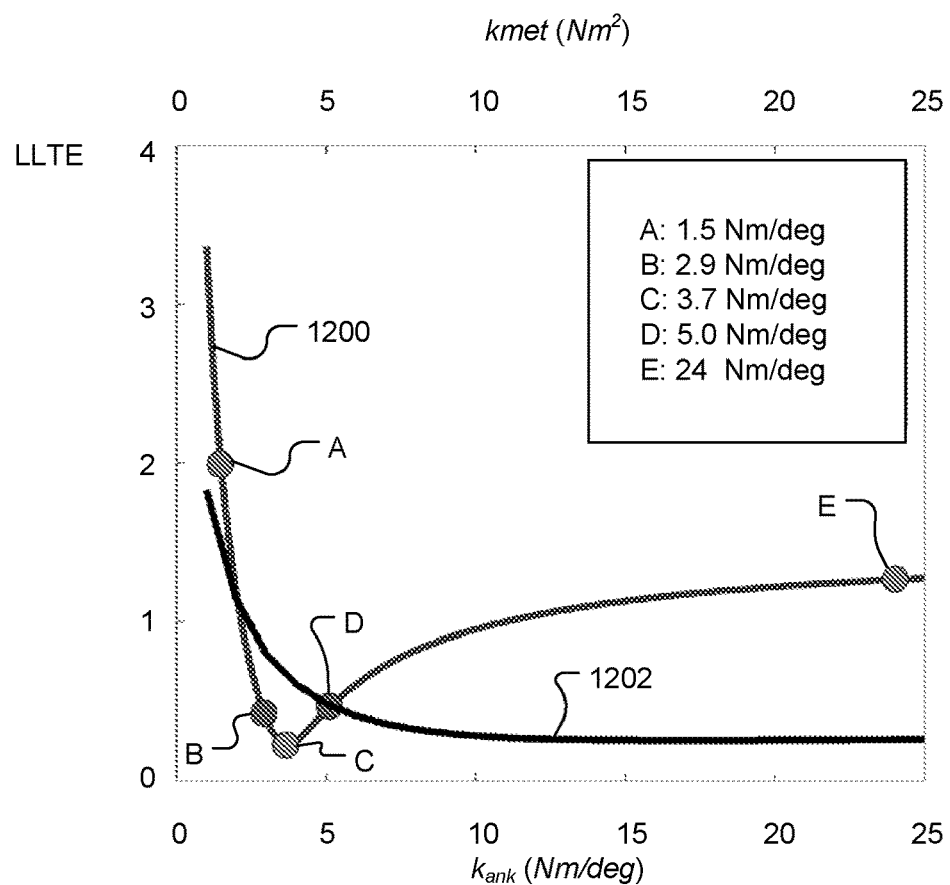
FIG. 12 is a graph illustrating: (a) dependence of a Lower Leg Trajectory Error (LLTE) value on ankle stiffness and (b) dependence of the LLTE value on forefoot beam stiffness, according to embodiments of the present invention.

In order to evaluate the LLTE as an optimization metric, it was necessary to design, build, and test prosthetic feet based on the optimal ankle and forefoot stiffnesses identified above. It is also important to understand the sensitivity of these stiffnesses on the foot's anticipated performance. Using the method presented by Olesnavage and Winter [Ref 4] and summarized above, the LLTE for this foot architecture (FIG. 11) was computed for each ankle and forefoot stiffness ranging from about 0.5 N·m/deg to about 25 N·m/deg and from about 1 N·m² to about 25 N·m², respectively. FIG. 12 plots the LLTE for varying forefoot stiffnesses at the optimal ankle stiffness and for varying ankle stiffnesses at the optimal forefoot stiffness. It also shows that the LLTE value is much more sensitive to the ankle stiffness than the forefoot beam stiffness.

We chose to fabricate five ankle stiffnesses that range from about 1.5 to about 24 N·m/deg to test in this study, which span an order of magnitude of LLTE values. Three of the five stiffnesses were chosen at: optimum, slightly stiffer than optimum and slightly less stiff than optimum. Two of the five stiffnesses were chosen to yield much higher LLTE values, near the asymptotic limits, but still feasible to manufacture. The chosen range of ankle stiffnesses spans a similar range as ankle quasi-stiffness data from normal walking, which have been estimated as roughly 1.5 to 6.3 N·m/deg [Ref 9], 3.5 to 17.3 N·m/deg [Ref 10], or 3.5 to 24.4 N·m/deg [Ref 8] during different phases of gait.

FIG. 12 is a graph illustrating: (a) dependence of the LLTE value on ankle stiffness $k_{ank}$ and (b) dependence of the LLTE value on forefoot beam stiffness $k_{met}$. Sensitivity of the ankle rotational stiffness on the LLTE value for the optimal value of $k_{met}$ of about 16.0 N·m² is shown by plot 1200, and sensitivity of the forefoot beam stiffness on the LLTE value for the optimal $k_{ank}$ of about 3.7 N·m/deg is shown by plot 1202. The minimum LLTE value was achieved for $k_{ank}$ is about 3.7 N·m/deg and $k_{met}$ is about 16.0 N·m². Five points A, B, C, D and E represent the five ankle stiffnesses selected to be fabricated as prototypes.

It should be noted that the ankle and forefoot stiffness at the minimum LLTE value has the most physical relevance. This configuration of the foot would be most likely to replicate near-physiological kinematics and kinetics. An ideal foot with LLTE=0 would facilitate a perfect replication. Since the LLTE is calculated using physiological GRFs as inputs, higher LLTE values, thus higher predicted kinematic errors, indicate that some sort of compensation by a user of the foot would be likely. These compensations could manifest as modified kinematics or kinetics.

A perspective view of this test foot 100 is shown in FIG. 1. The rigid structural components were machined from acetal resin. The ankle joint rotates about a steel pin 106. Custom machined nylon 6/6 flexural springs 114 and 116, fitted in aluminum mounts 118, 120, 138 and 700, control the ankle joint rotational stiffness. Other suitable materials may be used instead. The flexible forefoot 142 was made from nylon 6/6 and was fixed to the rigid acetal resin structure with machine screws inserted into tapped holes in the acetal resin. As built, the experimental device has an average mass of about 1.1 kg, which is approximately 52% less than the mass of our previous prototypes [Ref 6] and similar to the mass of a human foot, which is about 1.45% of body weight [Ref 5] or about 0.82 kg for a 56.7 kg person. The nylon springs 114 and 116 facilitated the substantial mass reduction.

Spring Design Requirements

The entire foot mechanism should be compact and lightweight, so that it does not interfere with gait. The foot mechanism also should be modular, so that the ankle stiffness can be changed quickly by exchanging different springs 114 and 116. These requirements immediately preclude use of commercially available coil springs, as existing coil springs of sufficient stiffness and range of motion are too heavy and bulky to allow interchangeability. The springs 114 and 116 described herein are able to withstand a moment of at least about 105 N·m before yield, corresponding to the case in which a 56.7 kg user applies her body weight on the tip of the prosthesis toe. These loads required a material with a high yield strain $$\sigma_{yield} = \frac{\sigma_y}{E}$$

where $\sigma_y$ and E are the yield strength and elastic modulus of the material, respectively), and a high strain energy density ($u=(\sigma_y^2)/E$). Nylon 6/6 exhibits good characteristics for a readily available, easy to machine material, with a strain energy density of about 1.77 kJ/kg and a yield strain of about 0.034 (McMaster-Carr Inc., Elmhurst, Ill.). For the chosen ankle stiffness values (about 1.5, 2.9, 3.7, 5, and 24 N·m/deg (FIG. 12)), the ankle should exhibit high ranges of motion, up to about 30 degrees or more, similar to biological ankles, in order to replicate the expected lower leg trajectory.

Maximization of Strain Energy

The stiffness and range of motion requirements for the ankle spring exceed possible values for most common springs, even packaged leaf springs called flexural springs, which would commonly be used for a device of this size. Therefore, the inventors considered how to best maximize strain energy stored in a spring. We realized a beam-type architecture for the springs would facilitate manufacture and modifying stiffness with geometric changes, and maximize strain energy stored in the springs.

Figure 13:
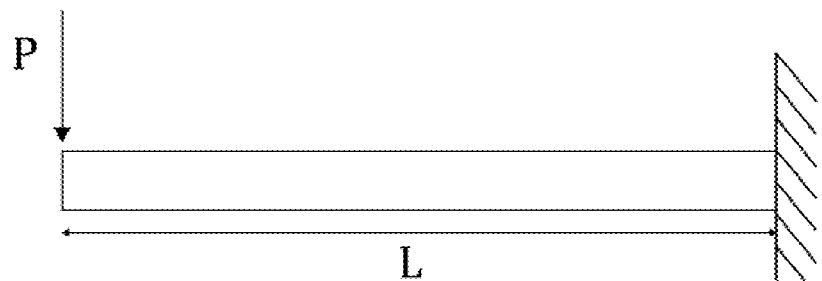
FIG. 13 is a schematic diagram of a cantilevered beam of length L under a load P, according to the prior art.
Figure 14:
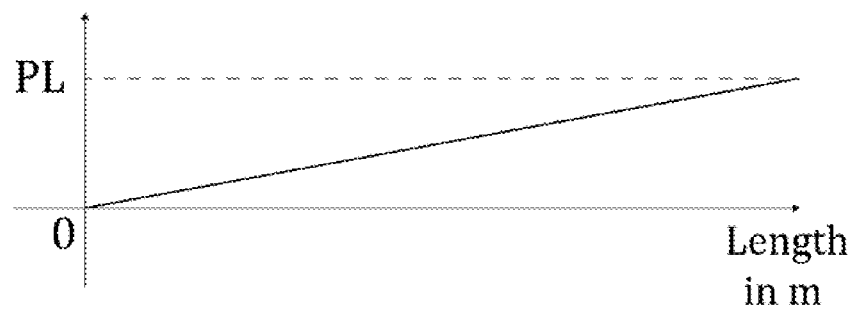
FIG. 14 is a graph of a moment in the cantilevered beam of FIG. 13, according to the prior art.

In a beam, the material yields under a stress $\sigma_y$ corresponding to a maximum moment $M_y$ applied to the beam. In a typical cantilevered beam bending scenario, the moment varies linearly from the tip to the base of the beam. FIG. 13 is a schematic diagram of a beam of length L under a load P. FIG. 14 is a graph of a moment in the beam of FIG. 13.

The maximum moment, and thus the maximum strain energy stored per volume in the beam (for a constant cross section), occurs only at the base. The strain energy u is $$u \sim \frac{\sigma^2}{E} \sim \frac{(My)^2}{EI^2} \quad (2)$$

where E is the modulus of elasticity, I is the area moment of inertia, and y is the distance from the neutral axis.

Figure 15:
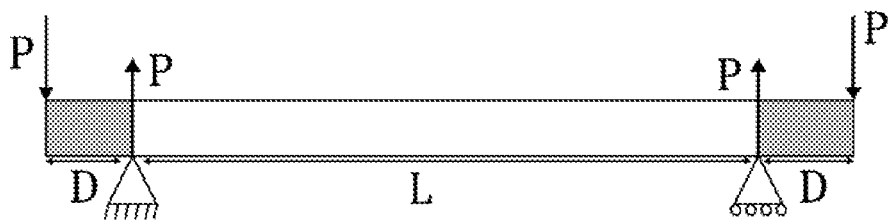
FIG. 15 is a schematic diagram of a four-point beam under a load, according to the prior art.
Figure 16:
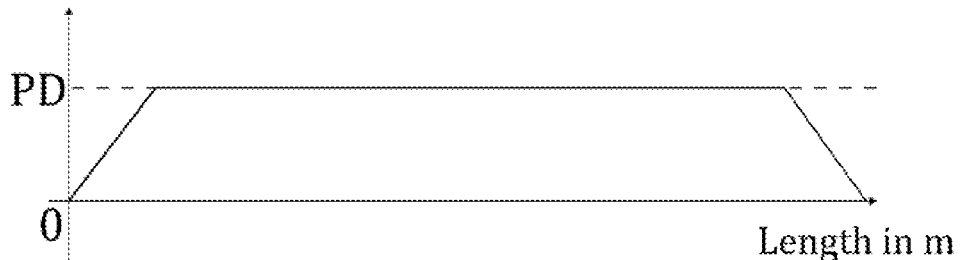
FIG. 16 is a graph of a moment in the four-point beam of FIG. 15, according to the prior art.

No strain energy is stored at the tip of the beam, and thus the tip of the beam presents wasted strain energy storage potential. To maximize the strain energy stored in a beam of constant cross section, a uniform moment of $M_y$ must be applied along the entire beam length. We realized this can be achieved, or at least approximated, using a four-area beam bending scenario with rigid extremities, such as those provided by spring mounts 118 and 120. A beam loaded in this manner is able to store approximately four times as much elastic energy as a cantilevered beam of the same length and cross section. FIG. 15 is a schematic diagram of a four-point bending beam, as viewed in profile (side view), of length L with rigid extremities of length D, under a load P. D corresponds to beam length outside each of two vertical supports. FIG. 16 is a graph of a moment in the beam of FIG. 15.

In a four-point bending beam, force is applied at four points, as viewed in profile, as shown schematically in FIG. 15. Thus, in a practical four-point bending beam with a non-zero width, each force is applied at one or more points and/or along one or more lines, all of which are disposed along a line that extends laterally across the beam, i.e., perpendicular to the longitudinal axis of the beam, as the beam is viewed isometrically. In profile, all the points and/or lines where one of the four forces is applied are visible as a single point.

Figure 17:
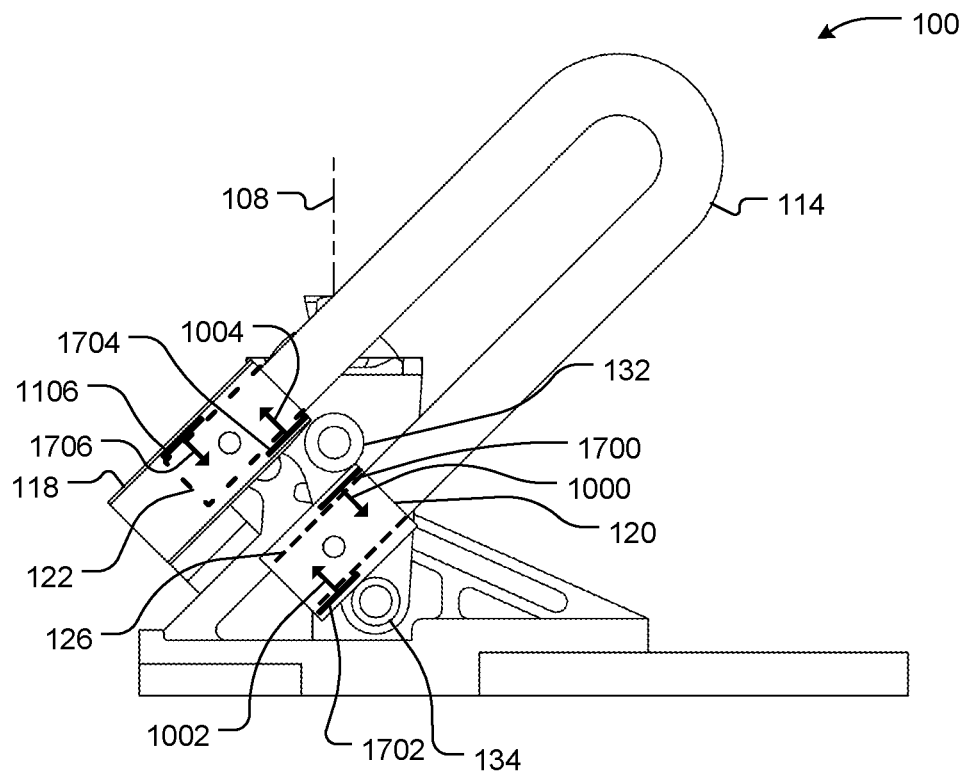
FIG. 17 is a side view of the prosthesis of FIGS. 1-3, similar to FIG. 10, schematically illustrating areas of force applied when the prosthetic ankle bends, in a four-area bending scenario, according to an embodiment of the present invention.

However, in a "four-area bending beam," any of the four forces may be applied within a respective area on the beam. That is, each force is not limited to being applied along a line extending laterally across the beam. In other respects, a four-area bending beam is similar to a four-point bending beam. FIG. 17, which is similar to FIG. 10, schematically illustrates edge views of four areas 1700, 1702, 1704 and 1706, where the four forces 1000-1006 are applied to the U-shaped spring 114 in a four-area bending scenario. Each of the four forces 1000-1006 may be applied to the spring mounts 118 and 120 at respective points or lines, for example along lines of contact between the respective bearings 132 and 134 and the spring mount 120. The spring mounts 118 and 120 distribute the forces 1000-1006 across respective areas 1700-1706 on the U-shaped spring 114. Size, placement and shape of each respective area 1700-1706 depends, at least in part, on size and shape of the respective spring mount 118 or 120 and how tightly the respective terminal portion 122 or 126 of the U-shaped spring 114 fits within the respective spring mount 118 or 120.

Figure 18:
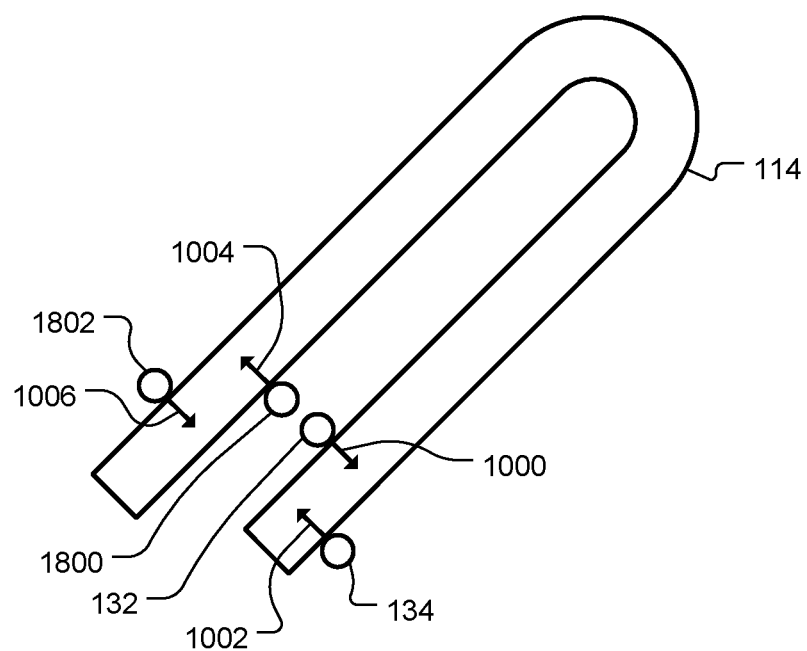
FIG. 18 is a side view of the U-shaped spring of FIGS. 1-3, 10 and 17, without any spring mount, according to another embodiment of the present invention.

One or both of the spring mounts 118 and/or 120 may, however, be omitted, such as to apply force, for example force 1000, 1002, 1004 and/or 1006, directly to the U-shaped spring 114 at a point or line, as in a four-point bending beam. For example, as schematically illustrated in FIG. 18, bearings 132 and 134 may bear directly on the U-shaped spring 114, and similar bearings or pins 1800 and 1802 may bear directly on the U-shaped spring 114, without any intervening spring mounts. Optionally, any combination of the bearings or pins 132, 134, 1800 and/or 1802 may be replaced by respective rigid mechanical connections between the U-shaped spring 114 and the prosthetic foot 102 or the prosthetic ankle 104 (not shown in FIG. 18). If none of the interfaces at which the forces 1000-1006 is applied to the U-shaped spring 114 includes a mechanical attachment between the U-shaped spring 114 and the prosthetic foot 102 or the prosthetic ankle 104, a separate holder or fastener (not shown) may be included to prevent loss of the U-shaped spring 114 when no or little force is applied. As used herein, the term "four-area bending beam" includes a four-point bending beam.

Packaging and Fabrication

To package a constant or nearly constant moment beam in the prosthetic foot, the four-area bending beam was arranged into a U-shape 114 or 116. FIG. 10 is a side view of the prosthesis 100 of FIGS. 1-3 schematically illustrating forces applied when the prosthetic ankle bends. P is a load applied to the beam, similar to the four-point bending beam scenario illustrated in FIG. 15, and $M_r$ is a reaction moment at the base.

This arrangement does not affect the force couple and moment reactions on each end of the beam, and to first order estimates, retains a constant or nearly constant moment applied over the entire beam length. In our design, the U-shaped springs 114 and 116 are held by aluminum mounts 118, 120, 138 and 700 that act as the rigid extremities and impose a rotation on the terminal portions 122 and 126 of the beam. These mounts 118, 120, 138 and 700 also enable the springs 114 and 116 to be easily exchanged. Changing the overall length and/or the width of the beam, or its material, varies the rotational stiffness of the ankle.

First-order calculations were performed using Euler-Bernoulli beam bending theory to design the U-springs 114 and 116. A relation between the rotational stiffness of the beam $k_{beam}$, its length L, thickness b, width w, Young's Modulus E, and yield stress $\sigma_y$ was derived using Eqs. (3)-(5).

The maximum moment $M_y$ under which the beam was loaded was derived from the yield stress of nylon 6/6, with a safety factor of 1.2 (Eq. (3)). Then, the maximum end slope of the beam was calculated from $M_y$, the Young's modulus of nylon 6/6 and the beam geometry (Eq. (4)). The end slope corresponds to half of the ankle angle $\theta_{ankle}$, since in the ankle reference, one of the terminal portions of the beam remains still. The rotational stiffness was then calculated as the moment divided by the ankle angle (Eq. (5)).

$$M_y = \frac{2I\sigma_y}{b} \quad (3)$$

$$\theta_{max} = \frac{M_y L}{2EI} = \frac{\theta_{ankle,max}}{2} \quad (4)$$

$$k_{ankle} = \frac{M}{\theta_{ankle}} = \frac{Ewb^3}{12L} \quad (5)$$

Figure 19:
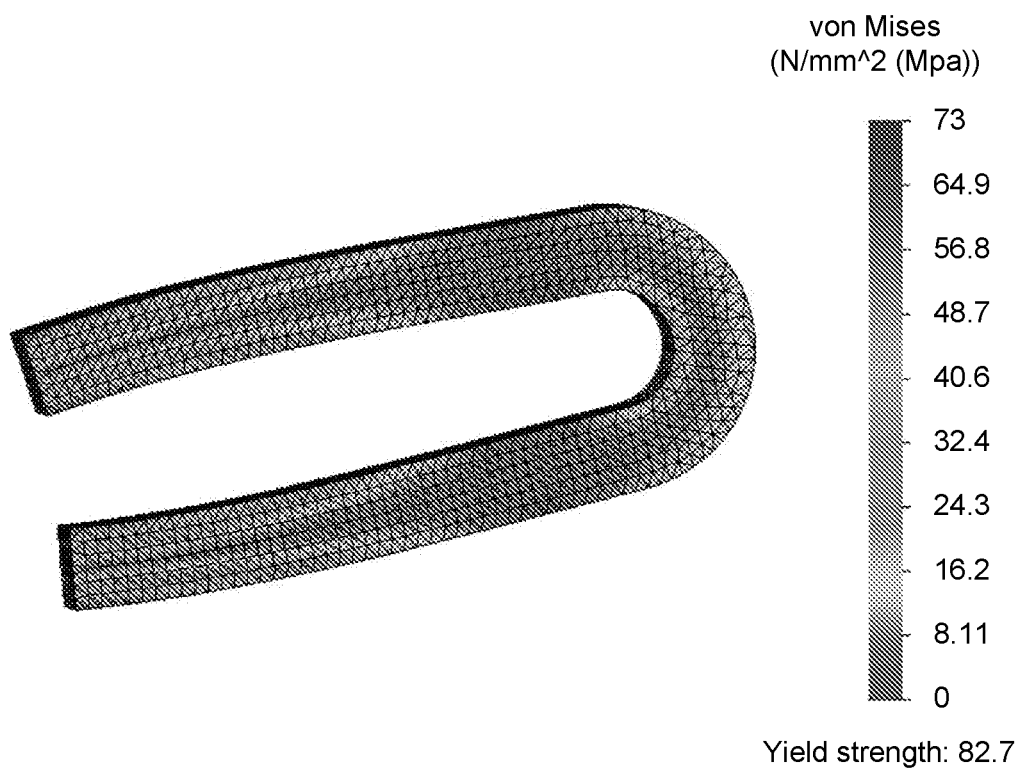
FIG. 19 is a computer-generated graph from a computer-based finite element analysis of the U-shaped spring of FIGS. 1-3 and 10, color coded to show von Mises stress distribution within the U-shaped spring, as the U-shaped spring undergoes a load of about 52.5 N·m, according to an embodiment of the present invention.

Using Eqs. (3)-(5), a first estimate of the beam geometries may be calculated to achieve the desired rotational stiffness with an applied moment of 105 N·m corresponding to the case in which a 56.7 kg user applies his body weight on the tip of the prosthesis toe, before yield. Because, in the embodiment described herein, the beams undergo large deformations, and the radius of curvature of the beam at the curve is on the same order of magnitude as the thickness of the beam, the U-shaped beam is stiffer than a straight beam of the same length. Therefore, finite element analysis (FEA) may be performed, such as using the Solidworks simulation tool (Dassault Systemes, Inc, Velizy-Villacoublay, France), to adjust the length of the U-shaped beam 114 or 116 from the Euler-Bernoulli solution to achieve the desired rotational stiffness (FIG. 19). The U-shaped beam 114 or 116 resulting from the finite element analysis is, on average, about 60% shorter than the first order estimate.

In one embodiment, U-shaped springs 114 and 116 that yield optimal ankle stiffness of about 3.7 N·m/deg have a thickness of about 18.2 mm, a width of about 14.0 mm and a length of about 160 mm. The length and width of the beams may be varied to achieve a desired range of ankle stiffnesses, such as corresponding to those reported in FIG. 12. Total mass of a pair of nylon U-shaped springs 114 and 116 is about 80 g to about 400 g. In one embodiment, about 3.7 N·m/deg U-shaped springs 114 and 116 weigh about 225 g. The springs 114 and 116 may be mounted at an angle (FIGS. 1-3 and 10), rather than vertically, to reduce the total foot volume and mass of the structure required to support them. However, the springs 114 and 116 may be mounted at other angles, such as vertical.

Cantilever Forefoot Design

The geometry of the beam forefoot 142 may be selected to replicate articulation of a physiological foot [Ref 5] by placing the approximate rotational axis during bending, calculated from the pseudo-rigid body model, at the same location as the metatarsal joint [Ref 7]. A width $w_b$ of about 58.0 mm and a length $l_b$ of about 70.0 mm may be used, so that the total length of the foot 100 is about 21 cm. To achieve a beam bending stiffness of $k_{met}$ of about 16.0 N·m², several materials may be used, such as acetal resin, nylon, polycarbonate, aluminum or steel. The beam thickness $h_b$ and maximum force $F_{max}$ that can be applied to the tip of the beam were derived from their Young Modulus E and yield stress $\sigma_y$ using the following equations.

$$k_{met} = \frac{Ew_b h_b^3}{12} \quad (5)$$

$$F_{max} = \frac{\sigma_y h_b^2 w_b}{6l_b} \quad (6)$$

From the desired stiffness values, we realized nylon 6/6 could withstand the highest load before yielding. Thus, the beam forefoot 142 may be machined out of nylon 6/6, with a thickness $h_b$ of about 11.1 mm, to achieve a bending stiffness $k_{met}$ of about 16.0 N·m², while withstanding an about 612 N force, which corresponds to the maximum vertical ground reaction force (GRF) experienced during level ground walking [Ref 5], with a safety factor of 2.3.

Experimental Validation

Figure 20:
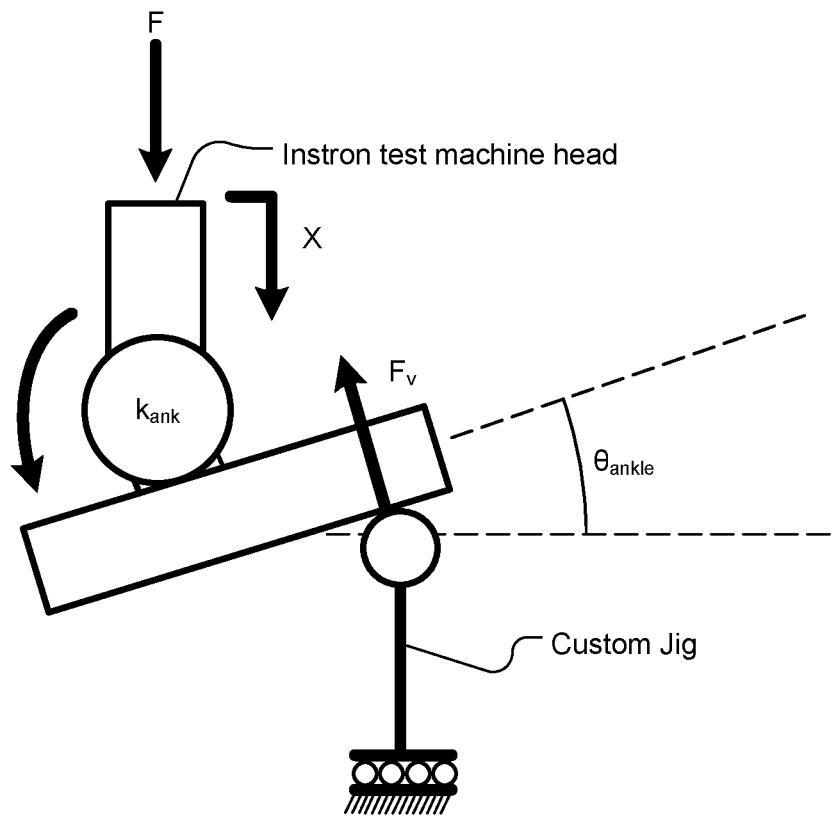
FIG. 20 is a schematic diagram of an experimental setup to measure ankle rotational stiffness, according to an embodiment of the present invention.

The ankle rotational stiffnesses were measured using an Instron load testing machine (Universal Testing System, Instron, Illinois Tool Works Inc., Norwood, Mass.). The experimental setup consisted of a jig constraining the test foot while the Instron machine loaded the rigid part of the forefoot 142, thus applying a moment on the ankle joint. FIG. 20 is a schematic diagram of an experimental setup to measure ankle rotational stiffness $k_{ank}$, as a result of an applied load F on the shank from the Instron load testing machine, with the foot constrained in a vice. M is a resulting moment on the ankle, and $\theta_{ankle}$ is a measured ankle angle.

The Instron load cell was resistant to off-axis loading errors, with a force measurement error of about 4.4% for this experiment. The foot was loaded at a constant rate of about 300 mm/min. until a moment of approximately 90 N·m was achieved on the ankle, corresponding to the maximum ankle moment experienced during flat ground walking from the Winter's data [Ref 5], or the maximum ankle angle computed during the LLTE calculation of the specific ankle spring was achieved. The vertical load and displacement were recorded at a rate of about 10 Hz.

A custom jig fixed on the Instron machine included a linear stage on which an aluminum rod is mounted on a set of bearings. The foot is then loaded on the rigid part of the forefoot through the aluminum rod, so that the load remains perpendicular to the foot at the contact point. The linear stage enables us to choose a position at which the vertical loads are applied.

The acetal foot structure on which the loads were applied is considered rigid in respect to the ankle springs since, under a moment of about 90 N·m, the resulting deformation lead to an ankle angle error of about 0.45 degrees, which is negligible compared to the ankle spring range of motions tested here (about 5 to about 25 degrees). The load and displacement data were then converted using geometric relations (FIG. 21) into ankle moment and angle data. Equation (8) was first solved to get the ankle angle θ, and then Eqs. (9) and (10) were used to compute the ankle moment M $$\sin\theta(d - r\sin\theta - (e - x + r(1 - \cos\theta)\tan\theta)) = e - \frac{e - x + r(1 - \cos\theta)}{\cos\theta} \quad (8)$$

$$F_v \cos(\theta) = F_i \quad (9)$$

$$M = F_v d_m = F_i(d - r\sin\theta - (e - x + r(1 - \cos\theta)\tan\theta) \quad (10)$$

The U-shaped springs 114 and 116 all exhibited constant or nearly constant linear stiffnesses ranging from about 1.5 to about 24 N·m/deg, as desired. The U-spring experimental data are plotted in FIG. 22 showing rotational stiffnesses of about 1.5, 2.9, 3.6, 4.9, and 24 N·m/deg.

Figure 22:
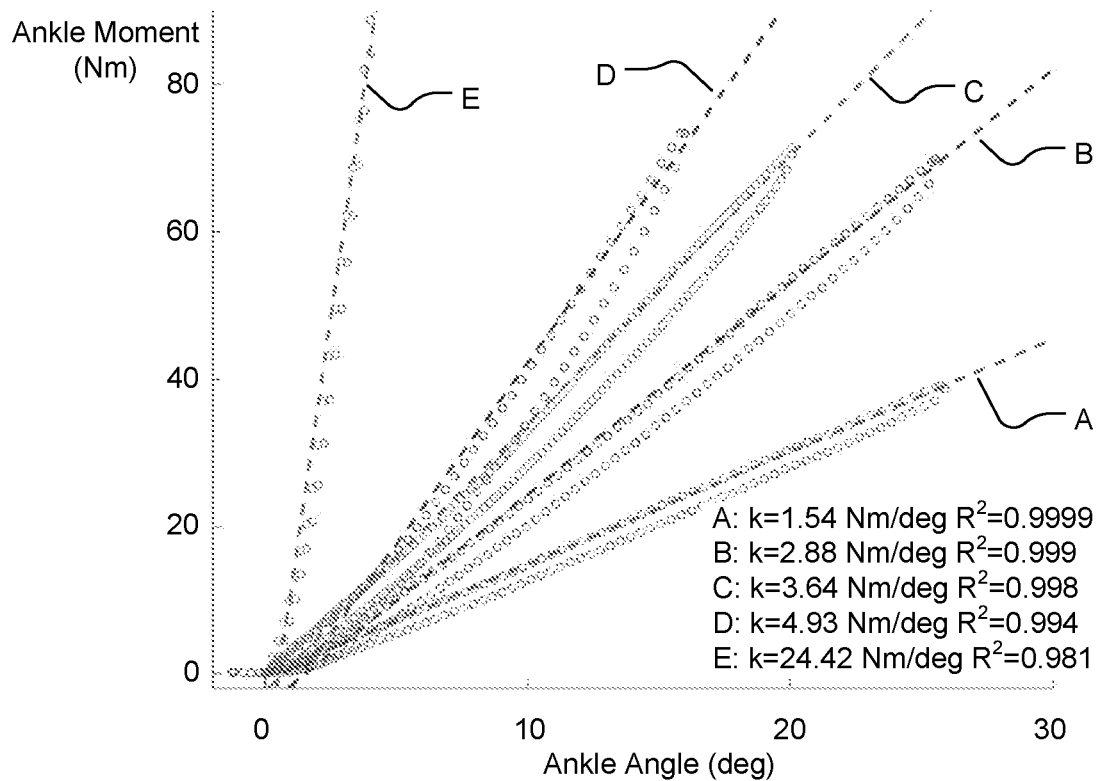
FIG. 22 is a graph plotting experimental data collected from the experimental setup of FIG. 20, and derived according to the geometric relations of FIG. 21, from testing a prototype of the prosthesis of FIGS. 1-3 and 10 with a variety of spring stiffnesses, compared to values predicted by finite element analysis, according to respective embodiments of the present invention.

FIG. 22 is a graph plotting experimental data, represented by circles, from testing a prototype of the prosthesis 100 with a variety of spring stiffnesses identified as A, B, C, D and E. The two lines of circles of each letter (A, B, C, etc.) represent respective loading and unloading of the prototype. As discussed herein, some energy is dissipated in the springs 114 and 116; hence the unloading lines do not exactly match the loading lines. The stiffness of the springs 114 and 116 is defined from the loading process. Dashed lines represent linear fits to the experimentally collected loading data. The linear fit lines generally agree with rotational stiffness values of the springs as predicted by finite element analysis. The springs 114 and 116 exhibited some hysteresis, due to viscous flow in the material.

As can be seen from FIG. 22, the linear fits of the experimental data agree with the finite element analysis for the rotational stiffness values with an about 3% error and an average $R^2$ value of about 0.994. The energy storage and return efficiency of these springs 114 and 116 was, on average, about 88% (Table 1).

TABLE 1

Ankle U-spring efficiencies, ratios between stored and returned energy

| Spring stiffness (N · m/deg) | 1.54 | 2.88 | 3.64 | 4.93 | 24.4 |
|---|---|---|---|---|---|
| Efficiency (%) | 89.0 | 89.4 | 88.1 | 83.7 | 89.4 |

Figure 21:
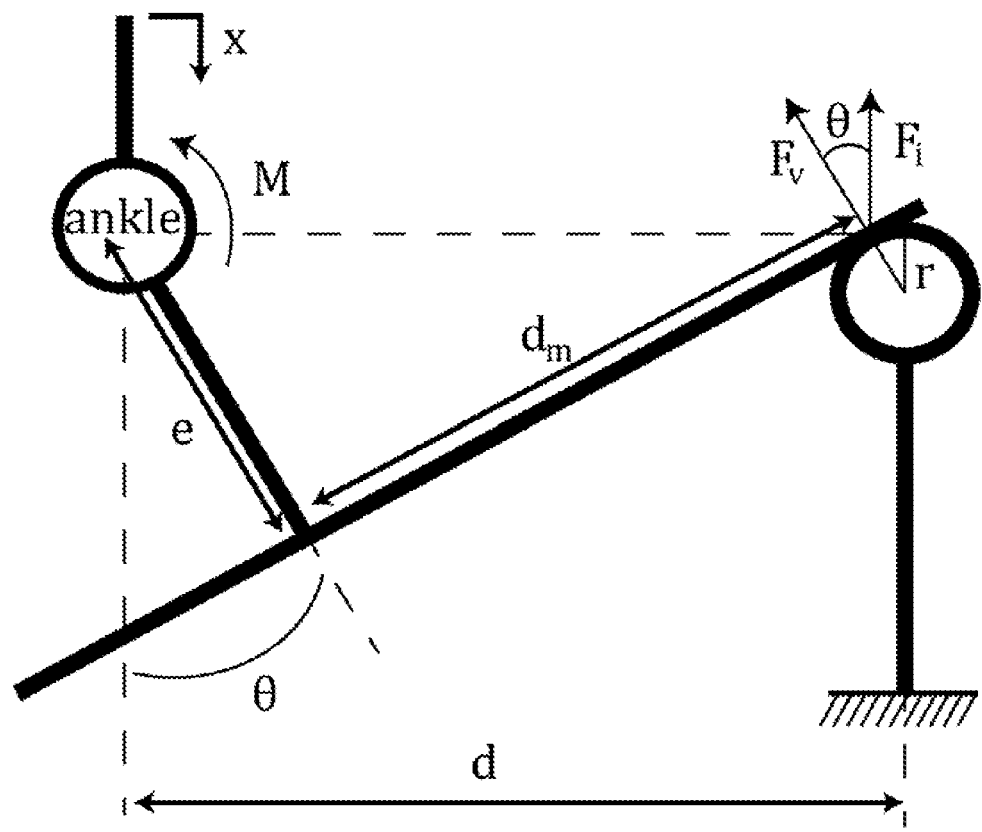
FIG. 21 is a schematic diagram of geometric relations used to convert experimental load and displacement data (x, $F_i$) collected from the experimental setup of FIG. 20 into ankle angle and moment data (M, θ), according to an embodiment of the present invention.

This reduced efficiency is most likely due to viscous flow in the material and friction losses at the ankle pin joint. The friction losses at the steel ankle pin 106 (FIGS. 1-3 and 10) were estimated on average to account for about 26% of the total dissipated energy. The work done by dynamic friction (Eq. (11)) was computed using loading and angular data collected from the Instron testing machine, the steel pin radius $r_s$ of about 4.8 mm and an acetal resin/steel dynamic coefficient of friction of $\mu_d$ of about 0.3 (FIG. 21).

$$W_{friction} = \int \mu_d F_v r_s d\theta_{ankle} \quad (11)$$

The experimental testing of the foot presented earlier ensures accurate agreement between the stiffness values calculated with our LLTE design optimization method and the actual performance of the experimental prototype. The ankle stiffness ranged from about 1.5 to about 24 N·m/deg and exhibited ranges of motion of up to about 30 degrees or more. While a biological ankle also allows an about 30 degree dorsiflexion of the foot [Ref 11], commercially available feet have a more limited range of motion. The SACH foot exhibits an about 10 degree dorsiflexion for a stiffness of about 16.3 N·m/deg [Refs. 11, 12], the rolling foot designed by Quesadag at the University of Louisville enables an about 16 degree ankle range of motion for a stiffness of about 3.8 N·m/deg [Ref 12], and the Seattle Ankle/Lite Foot and the Flex-Foot Assure allow an about 20 degree dorsiflexion for an ankle stiffness of approximately 4.9 N·m/deg [Refs. 11, 12]. The designed experimental foot 100 exhibits high ankle stiffnesses along with high ankle ranges of motion, similar to those of a physiological foot, and beyond those of common commercial products.

Preliminary Testing

The test foot was first tested using pseudo-prosthesis boots to ensure that both the compliant elements and the foot could withstand typical loads experienced during flat-ground walking. The foot 100 and different U-shaped springs 114 and 116 were then tested on below-knee amputees (FIG. 2), who represent target users of the high-performance, low-cost prosthetic limb technology we aim to produce through our research program. Initial testing analyzed comfort, functionality, spring interchangeability, reliability and structural integrity of the foot to determine its suitability for use in clinical gait analysis studies, and possible future clinical trials. The test foot was fitted on three male subjects with unilateral transtibial amputations who have been long-time users of a commercially available prosthesis. The subjects had body masses ranging from about 55 kg to about 65 kg. Apart from the amputations, the subjects had no further pathologies. The subjects were asked to walk on flat ground using the prototype until they felt comfortable with it, at which point they were asked to walk up and down stairs and ramps.

Our prototype feet withstood several hours of testing on multiple subjects, using multiple ankle springs 114 and 116, and experienced no mechanical issues. The springs 114 and 116 could be exchanged within a matter of minutes without removing the foot from the patient's prosthetic limb. The weight of the prosthesis was not a concern for the users, and no additional issues were raised during testing. The subjects then completed surveys describing qualitatively what they liked and disliked about the prototype. Subjects liked the energy storage and return of the prototype and the increased walking speed. Dislikes mainly focused on aesthetics of the foot 100, which may be addressed in future iterations with cosmetic coverings or reorienting the U-shaped springs 114 and 116. This positive feedback from preliminary testing was compelling enough to warrant further refinement of the foot design and its use for clinical studies.

In Vivo Testing

To further assess the mechanical behavior of the experimental prosthetic foot, in vivo testing was conducted at the Jesse Brown VA Medical Center Motion Analysis Research Laboratory in collaboration with the Northwestern University Prosthetics Orthotics Center. The foot was fitted to a transtibial subject who weighed 54.2 kg and measured 169 cm tall. This subject was chosen because her body mass and size were similar to that of the subject reported in Winter's gait data [Ref 5], which was used as inputs to our LLTE design optimization.

Figure 23:
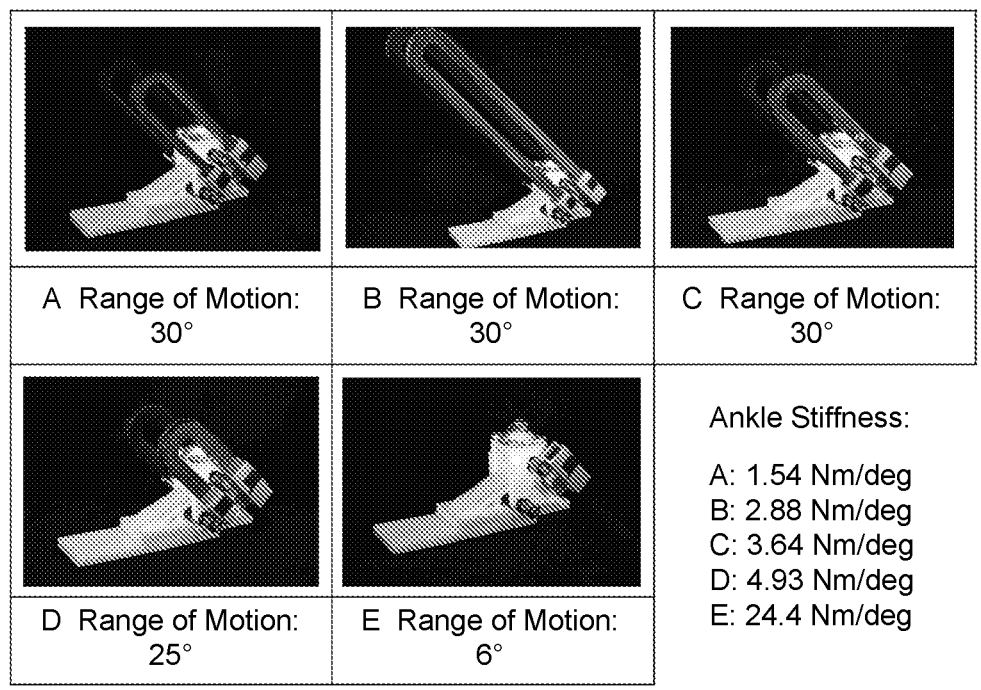
FIG. 23 illustrates five tested prototypes of the prosthesis of FIGS. 1-3 and 10, with a variety of spring stiffnesses and corresponding ranges of motion values achieved, according to respective embodiments of the present invention.

The subject tested each of the five ankle stiffnesses produced in this study. For each ankle stiffness, she was asked to walk on flat ground using the prototype until she felt comfortable. After about 10 minutes using the prototype, the subject walked at a comfortable, self-selected speed on a walkway, during which gait kinematic and kinetic data were recorded for at least five steps. The five different rotational ankle stiffness conditions tested (FIG. 23) are labeled A through E, where A represents the most compliant spring 114 or 116 and E represents the stiffest. For condition E, no U-shaped spring was used. Instead, the prosthetic talocrural joint was locked, i.e., the prosthetic foot 102 was mechanically locked to the prosthetic ankle 104. Thus, any bending was as a result of deformation of the prosthetic foot 102 and/or the prosthetic ankle 104 materials.

The ankle springs 114 and 116 were changed on the prosthesis in a random order to avoid any biases from the subject. There was no need of any realignment between the socket and the foot, because the foot remained firmly attached to the socket pylon during the entire process. The participant could rest as needed between each pair of conditions. Kinematic data were recorded through a motion capture system (Motion Analysis Corporation, Santa Rosa, Calif.), and kinetic data were measured by force plates (Advanced Mechanical Technology, Inc., Watertown, Mass.) embedded within the walkway. The entire set of data was then processed and analyzed through custom scripts implemented in MATLAB numerical computing environment (The MathWorks, Inc., Natick, Mass.).

Figure 24:
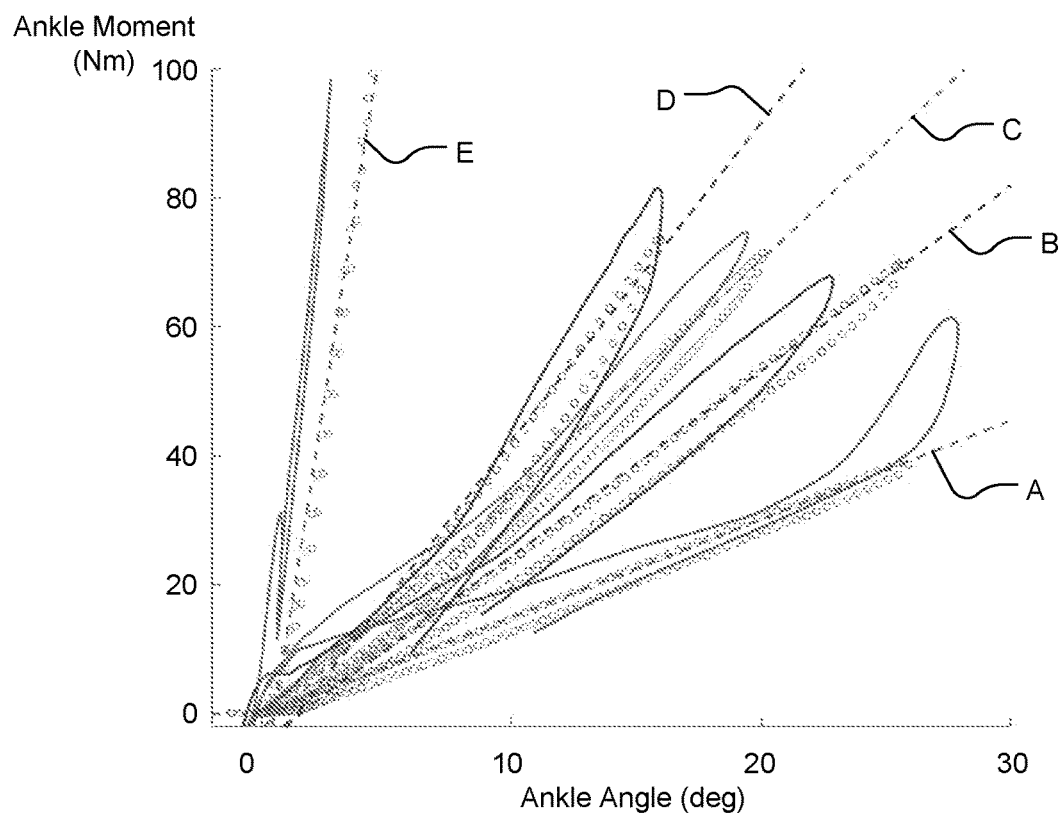
FIG. 24 is a graph of expected versus measured ankle stiffnesses of a prototype of the prosthesis of FIGS. 1-3 and 10 with various springs, according to respective embodiments of the present invention.

Stance phase ankle flexion moments and angles were computed from GRFs, center of pressure and reflective marker position for each step and each stiffness condition. The measured in vivo ankle moment versus angle behavior were averaged over all steps for each condition and plotted against the mechanical testing data from above. FIG. 24 is a graph of expected versus measured ankle stiffnesses of a prototype of the prosthesis 100 with various springs. Experimental data from testing the set of springs 114 and 116, labeled A-E corresponding to rotational stiffness of about 1.5, 2.9, 3.6, 4.9 and 24 N·m/deg, are plotted in solid line. Circle markers represent Instron test machine measured data, and dotted lines represent expected ankle stiffnesses.

The in vivo test data align well with the mechanical behavior of the foot as measured on the Instron material testing machine. During the controlled dorsiflexion phase of stance, the ankle angle-moment curves fit the Instron measurements with $R^2$ values of about 0.73, 0.92, 0.82, 0.96 and 0.85 for conditions A through E, respectively (FIG. 24). These results demonstrate that the analytical model of a purely rotational pin joint with a specified constant rotational stiffness used in this LLTE-based optimization adequately represents the actual in vivo mechanical behavior of the prosthetic foot prototype. Furthermore, the U-springs 114 and 116 performed as desired in a clinical setting and did not adversely affect the subject's torque-angle ankle response.

However, the curvature in the in vivo test data does show that ankle springs 114 and 116 exhibited larger hysteresis during terminal stance, i.e., unloading of the ankle springs, compared to the mechanical behavior of the foot as measured on the Instron machine. This is most likely due to viscoelastic effects of the nylon, as the unloading rate in the in vivo testing was much higher than during the Instron testing.

CONCLUSIONS

Discussed herein are physical design, mechanical characterization, preliminary user field testing, and in vivo stiffness measurements of a novel prosthesis architecture. The prosthesis 100 was able to accurately express stiffnesses calculated using our LLTE design optimization method, both in bench-top Instron and in vivo testing. These results are an important step in utilizing the LLTE optimization metric as a design tool to optimize prosthesis that can achieve desired kinematic and kinetic performance when worn by transtibial amputees.

The presented prosthesis architecture enables rapid reconfiguration of different ankle stiffnesses and is able to provide ankle quasi-stiffness and range of motion values similar to those of a physiological foot and beyond those of common commercial products. The U-springs 114 and 116 used in the ankle enable much higher strain energy density than could be obtained by cantilevered beams of the same length and volume. The presented spring design and prosthesis architecture may be of value to other researchers who require high-stiffness and high-range of motion ankle joints.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

REFERENCES

[Ref 1] Ziegler-Graham K, MacKenzie E J, Ephraim P L, Travison T G, Brookmeyer R. Estimating the Prevalence of Limb Loss in the United States: 2005 to 2050, Archives of Physical Medicine and Rehabilitation 2008; 89(3):422-9.
[Ref 2] Fisher E S, Goodman D C, Chandra A. Disparities in Health and Health Care among Medicare Beneficiaries: A Brief Report of the Dartmouth Atlas Project, Robert Wood Johnson Foundation 2008.
[Ref 3] Owings M, Kozak L J, National Center for Health S. Ambulatory and Inpatient Procedures in the United States, 1996. Hyattsville, Md.: U.S. Dept. of Health and Human Services, Centers for Disease Control and Prevention, National Center for Health Statistics, 1998.
[Ref 4] Olesnavage, K. M., and Winter, A. G., 2015, "Lower Leg Trajectory Error: A Novel Optimization Parameter for Designing Passive Prosthetic Feet," IEEE International Conference on Rehabilitation Robotics (ICORR), Singapore, August 11-14, pp. 271-276.
[Ref 5] Winter, D. A., 2009, Biomechanics and Motor Control of Human Movement, 4th ed., Wiley, Hoboken, N.J.
[Ref 6] Olesnavage, K. M., and Winter, A. G., 2015, "Design and Qualitative Testing of a Prosthetic Foot With Rotational Ankle and Metatarsals Joints to Mimic Physiological Roll-Over Shape," ASME Paper No. DETC2015-46518.
[Ref 7] Olesnavage, K. M., and Winter, A. G., 2016, "Design and Preliminary Testing of a Prototype for Evaluating Lower Leg Trajectory Error as an Optimization Metric for Prosthetic Feet," ASME Paper No. DETC2016-60565.
[Ref 8] Howell, L. L., 2001, Compliant Mechanisms, Wiley, New York.
[Ref 9] Rouse, E. J., Hargrove, L. J., Perreault, E. J., and Kuiken, T. A., 2014, "Estimation of Human Ankle Impedance During the Stance Phase of Walking," IEEE Trans. Neural Syst. Rehabil. Eng., 22(4), pp. 870-878.
[Ref 10] Shamaei, K., Sawicki, G. S., and Dollar, A. M., 2013, "Estimation of Quasi-Stiffness of the Human Hip in the Stance Phase of Walking," PLoS One, 8(12), p. e81841.
[Ref 11] Wagner, J., Sienko, L. P. T. S. T., Supan, C. P. O. D., and Barth, C. P. O., 1987, "Motion Analysis of SACH vs. Flex-Foot™ in Moderately Active Below-Knee Amputees," Clin. Prosthet. Orthot., 11(1), pp. 55-62.
[Ref 12] Lehmann, J. F., Price, R., Boswell-Bessette, S., Dralle, A., Questad, K., and Quest, K., 1993, "Comprehensive Analysis of Dynamic Elastic Response Feet: Seattle Ankle/Lite Foot Versus SACH Foot," Arch. Phys. Med. Rehabil., 74(8), pp. 853-861.
[Ref 13] Quesadag, P. M., Pitkin, M., Colvin, J., and Srinivasan, R., 2000, "Biomechanical Evaluation of a Prototype Foot/Ankle Prosthesis," IEEE Trans. Rehabil. Eng., 8(1), pp. 156-159.

What is claimed is:

1. A prosthesis comprising:
a prosthetic foot;
a prosthetic talocrural joint;
a prosthetic ankle pivotally coupled to the prosthetic foot by the prosthetic talocrural joint, a pivot axis defined by the prosthetic talocrural joint; and
a four-area bending beam comprising a first spring set, the first spring set comprising at least one spring, a first terminal portion of each spring of the first spring set being mechanically coupled via two of four areas of the four-area bending beam to the prosthetic foot, and a second terminal portion of each spring being mechanically coupled via the other two of the four areas of the four-area bending beam to the prosthetic ankle, the first spring set being configured to resiliently resist pivoting of the prosthetic ankle about the prosthetic talocrural joint, relative to the prosthetic foot.

2. A prosthesis according to claim 1, wherein each spring of the first spring set comprises a U-shaped spring.

3. A prosthesis according to claim 1, wherein each spring of the first spring set comprises a C-shaped spring.

4. A prosthesis according to claim 1, wherein each spring of the first spring set comprises a V-shaped spring.

5. A prosthesis according to claim 1, wherein each spring of the first spring set comprises nylon 6/6.

6. A prosthesis according to claim 1, wherein each spring of the first spring set comprises carbon fiber.

7. A prosthesis according to claim 1, wherein each spring of the first spring set comprises fiberglass.

8. A prosthesis according to claim 1, wherein the prosthetic foot comprises a relatively rigid foot structure and a relatively flexible prosthetic forefoot cantilevered in front of the foot structure, wherein the foot structure is more rigid than the prosthetic forefoot.

9. A prosthesis according to claim 8, wherein the prosthetic foot further comprises a relatively flexible prosthetic heel that is more flexible than the prosthetic forefoot.

10. A prosthesis according to claim 1, wherein the first spring set is detachably attached to the prosthetic foot and to the prosthetic ankle.

11. A prosthesis according to claim 1, wherein the first spring set is detachably attached to the prosthetic foot and to the prosthetic ankle via respective removable pins.

12. A prosthesis according to claim 1, further comprising:
at least one first spring mount mechanically coupled to the prosthetic foot, each first spring mount of the at least one first spring mount being configured to detachably receive a respective first terminal portion of a respective spring of the first spring set; and
at least one second spring mount mechanically coupled to the prosthetic ankle, each second spring mount of the at least one second spring mount being configured to detachably receive a respective second terminal portion of a respective spring of the first spring set.

13. A prosthesis according to claim 12, wherein each spring of the first spring set is detachably attached to the respective first and second spring mounts.

14. A prosthesis according to claim 12, wherein each spring of the first spring set is detachably attached to the respective first and second spring mounts via respective removable pins.

15. A prosthesis according to claim 1, wherein:
each spring of the first spring set has a respective stiffness, and the first spring set has a total stiffness equal to a sum of the respective stiffnesses of the at least one spring of the first spring set; the prosthesis further comprising:
a plurality of selectable replacement spring sets, each selectable replacement spring set of the plurality of selectable replacement spring sets comprising at least one replacement spring, each replacement spring having a respective stiffness, each selectable replacement spring set of the plurality of selectable replacement spring sets having a respective total stiffness equal to a sum of the respective stiffnesses of the respective at least one replacement spring of the selectable replacement spring set, each selectable replacement spring set having a total stiffness different from the total stiffness of each other selectable replacement spring set and different from the total stiffness of the first spring set.

16. A prosthesis according to claim 15, further comprising:
- at least one first spring mount mechanically coupled to the prosthetic foot, each first spring mount of the at least one first spring mount being configured to detachably receive a respective first terminal portion of a respective spring of the first spring set; and
- at least one second spring mount mechanically coupled to the prosthetic ankle, each second spring mount of the at least one second spring mount being configured to detachably receive a respective second terminal portion of a respective spring of the first spring set; wherein:
- each first and second spring mount is configured to detachably receive a respective first and second terminal portion of a selected respective replacement spring of the plurality of selectable replacement spring sets in replacement of the respective first and second terminal portion of the respective spring of the first spring set.

17. A prosthesis according to claim 15, wherein:
- the total stiffness of a least stiff selectable replacement spring set of the plurality of selectable replacement spring sets is at most about 2 N·m/deg; and
- the total stiffness of a most stiff selectable replacement spring set of the plurality of selectable replacement spring sets is at least about 16 N·m/deg.

18. A prosthesis according to claim 1, wherein the four-area bending beam has a substantially constant moment along its length.

19. A prosthesis according to claim 1, wherein the first spring set comprises at least two springs.

* * * * *